United States Patent
Hanada et al.

(10) Patent No.: US 10,365,108 B2
(45) Date of Patent: Jul. 30, 2019

(54) INFORMATION ACQUISITION METHOD, WIRELESS COMMUNICATION DEVICE, ELECTRONIC TIMEPIECE AND RECORDING MEDIUM

(71) Applicant: CASIO COMPUTER CO., LTD., Shibuya-ku, Tokyo (JP)

(72) Inventors: Takeshi Hanada, Tachikawa (JP); Tadashi Kojima, Musashimurayama (JP); Oh Takahashi, Nishitokyo (JP); Toyokazu Nishio, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 15/900,417

(22) Filed: Feb. 20, 2018

(65) Prior Publication Data

US 2018/0245921 A1    Aug. 30, 2018

(30) Foreign Application Priority Data

Feb. 28, 2017  (JP) .................................. 2017-036054

(51) Int. Cl.
| | | |
|---|---|---|
| *H04W 24/00* | (2009.01) | |
| *G01C 21/00* | (2006.01) | |
| *H04W 4/02* | (2018.01) | |
| *G01S 19/01* | (2010.01) | |
| *H04B 1/3827* | (2015.01) | |
| *G04R 60/10* | (2013.01) | |

(52) U.S. Cl.
CPC ............ *G01C 21/005* (2013.01); *G01S 19/01* (2013.01); *H04W 4/025* (2013.01); *G04R 60/10* (2013.01); *H04B 1/385* (2013.01)

(58) Field of Classification Search
USPC ................ 701/431; 455/456.1, 41.2; 368/10
See application file for complete search history.

(56) References Cited

U.S. PATENT DOCUMENTS

| | | | |
|---|---|---|---|
| 2012/0316777 A1* | 12/2012 | Kitta .................. | G01C 21/3661 701/431 |
| 2013/0051186 A1 | 2/2013 | Honda et al. | |
| 2014/0073255 A1 | 3/2014 | Kuscher et al. | |
| 2014/0287686 A1* | 9/2014 | Kobayashi .............. | H04W 4/80 455/41.2 |

(Continued)

FOREIGN PATENT DOCUMENTS

| | | |
|---|---|---|
| JP | 2000180197 A | 6/2000 |
| JP | 2011139352 A | 7/2011 |

(Continued)

*Primary Examiner* — David Q Nguyen
(74) *Attorney, Agent, or Firm* — Holtz, Holtz & Volek PC

(57) ABSTRACT

There is provided an information acquisition method of a wireless communication device including a receiver configured to perform wireless communication with another wireless communication device to acquire information. The information acquisition method includes acquiring operation time information indicative of time at which the other wireless communication device receives an information acquisition instruction by an operation, acquiring position information indicative of a user position at time based on the acquired operation time information, and acquiring map information for indicating, on a map, the acquired position information.

17 Claims, 13 Drawing Sheets

(56) References Cited

U.S. PATENT DOCUMENTS

| | | | |
|---|---|---|---|
| 2015/0029826 A1* | 1/2015 | Antognini | G04G 9/0064 368/10 |
| 2015/0286190 A1 | 10/2015 | Honda et al. | |
| 2016/0048109 A1 | 2/2016 | Honda et al. | |
| 2016/0231711 A1 | 8/2016 | Honda et al. | |

FOREIGN PATENT DOCUMENTS

| | | | |
|---|---|---|---|
| JP | 2013050341 A | 3/2013 |
| JP | 2015534747 A | 12/2015 |

\* cited by examiner

INFORMATION ACQUISITION METHOD, WIRELESS COMMUNICATION DEVICE, ELECTRONIC TIMEPIECE AND RECORDING MEDIUM

CROSS-REFERENCE TO RELATED APPLICATION

This application is based upon and claims the benefit of priority from Japanese Patent Application No. 2017-036054, filed on Feb. 28, 2017, the entire contents of which are incorporated herein by reference.

BACKGROUND

The present disclosure relates to an information acquisition method, a wireless communication device, an electronic timepiece and a recording medium.

In recent years, there has been known a portable wireless communication device configured to receive and display map information for indicating a current position on a map. Also, there has been known an electronic timepiece configured to receive a radio wave from a satellite and to acquire position information indicative of a current position so as to correct a time measured in the own device.

For example, JP-A-2013-50341 discloses a wristwatch-type electronic timepiece configured to correct internal time information based on a satellite signal transmitted from a satellite. When a button for displaying position information is pushed, the electronic timepiece displays, as position information indicative of a current position, latitude and longitude, which are calculated based on the satellite signal transmitted from the satellite, by a pointer rotatable on a dial plate.

According to the electronic timepiece of JP-A-2013-50341, a user can know the latitude and longitude as the position information indicative of the current position by pushing the button of the electronic timepiece. However, even when the user operates the electronic timepiece, map information, with which the position information is indicated on a map, cannot be obtained.

In the meantime, according to a portable wireless communication device, map information for indicating a current position on a map can be acquired and displayed. However, the wireless communication terminal having such a function is larger than a wristwatch-type electronic timepiece, and it is complex to operate it.

For example, when a user takes out the wireless communication device and performs an operation of acquiring the map information, more action and time are required, so that the operability is low.

SUMMARY

An information acquisition method, a wireless communication device, an electronic timepiece and a recording medium are disclosed.

According to an illustrative embodiment of the present disclosure, there is provided an information acquisition method of a wireless communication device including a receiver configured to perform wireless communication with another wireless communication device to acquire information. The information acquisition method includes an operation time information acquisition step of acquiring operation time information indicative of time at which the other wireless communication device receives an information acquisition instruction by an operation, a position information acquisition step of acquiring position information indicative of a user position at time based on the operation time information acquired in the operation time information acquisition step, and a map information acquisition step of acquiring map information for indicating, on a map, the position information acquired in the position information acquisition step.

BRIEF DESCRIPTION OF THE DRAWINGS

The above and other aspects of the present invention will become more apparent and more readily appreciated from the following description of exemplary embodiments of the present invention taken in conjunction with the attached drawings.

DETAILED DESCRIPTION

Hereinafter, illustrative embodiments will be described with reference to the drawings.

In a first illustrative embodiment, map information is immediately acquired when a proximity operation is performed to an electronic timepiece. In a second illustrative embodiment, a plurality of times at which a proximity operation is performed to the electronic timepiece are stored and a smart phone receives the plurality of times and acquires map information corresponding to each time. In a third illustrative embodiment, the electronic timepiece receives a satellite radio wave and has various sensors. Meanwhile, in the description below, it is assumed that the smart phone and the electronic timepiece have been already paired (mutually authenticated).

(First Illustrative Embodiment)

Figure 1:
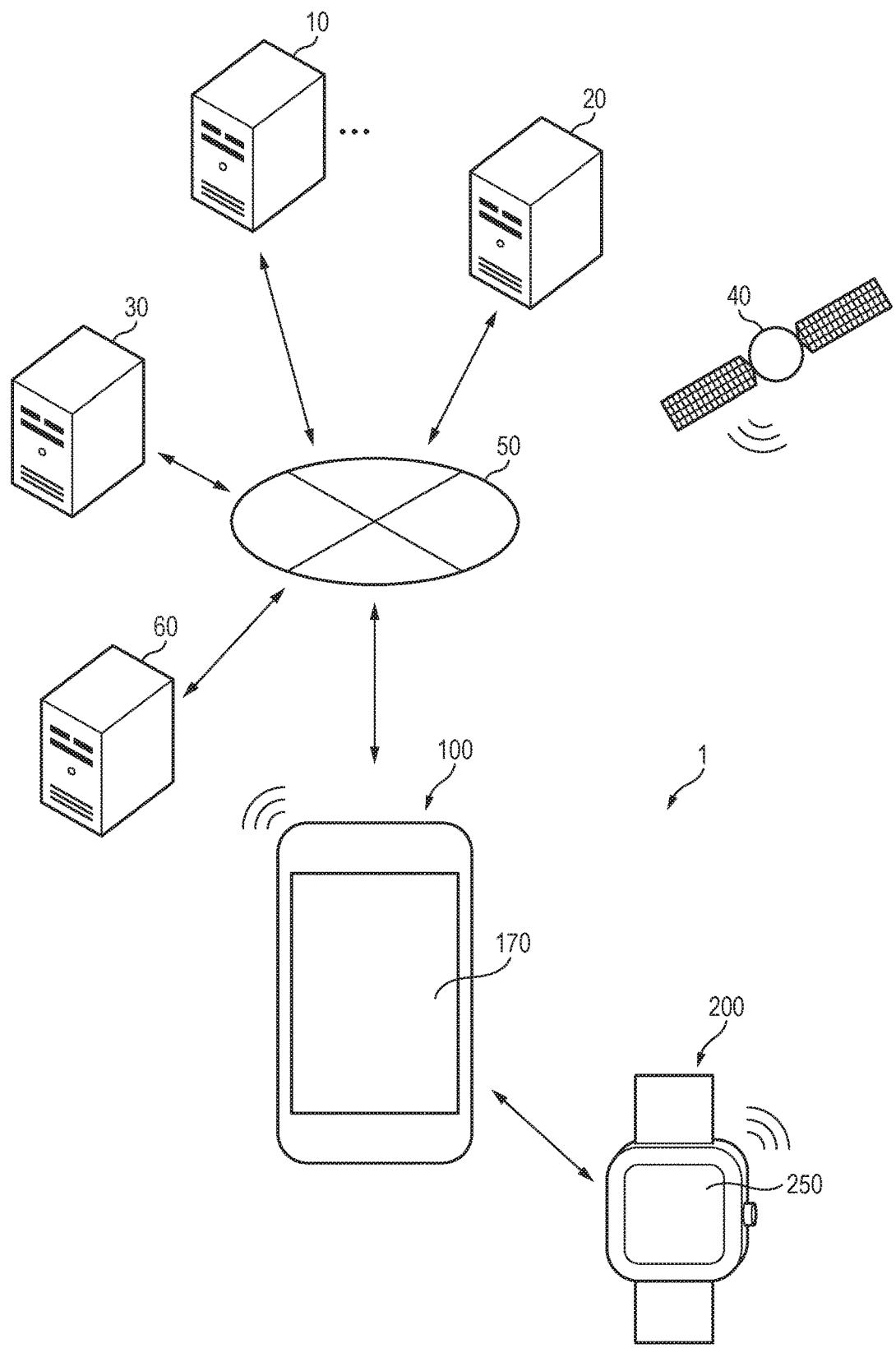
FIG. 1 illustrates a using manner of a communication system according to a first illustrative embodiment.

As shown in FIG. 1, a communication system 1 according to a first illustrative embodiment of the present disclosure includes a smart phone 100 which is a wireless communication device, and an electronic timepiece 200 which is a wireless communication device different from the smart phone 100.

The smart phone 100 and the electronic timepiece 200 are configured to perform near-field wireless communication based on Bluetooth (registered trademark) Low Energy (hereinafter, referred to as 'BLE'). The BLE is a standard (mode) designed for low power consumption in a near-field wireless communication standard referred to as Bluetooth.

The smart phone 100 is configured to operate as a central for receiving an advertise packet based on the BLE. The electronic timepiece 200 is configured to operate as a peripheral for transmitting an advertisement based on the BLE. During wireless communication after connection is established between the smart phone 100 and the electronic timepiece 200, the smart phone 100 operates as a master, and the electronic timepiece 200 operates as a slave.

The smart phone 100 is configured to receive a radio wave from a satellite 40. The satellite 40 is a satellite which is used for positioning in a Global Positioning System (GPS), a Global Navigation Satellite System (GLONASS) and the like, for example.

The smart phone 100 is configured to perform communication with other devices connected to a World Area Network (WAN) 50, via a relay device, an access point and the like (not shown). The other devices include a plurality of Network Time Protocol (NTP) servers 10 configured to provide time information, a Network Time Protocol-Pool (NTP pool) server 20, a location server 30 configured to provide information indicative of a position (latitude and longitude) of a communication terminal, and a map information distribution server 60 configured to provide map information.

The NTP pool server 20 is configured to receive an access from a communication terminal and to specify a position of the communication terminal by referring to a position database for an Internet Protocol (IP) of the communication terminal. The NTP pool server 20 is configured to allot NTP server(s) 10, which correspond to the position of the communication terminal, of the plurality of NTP servers 10. In general, a plurality of (for example four) NTP servers 10 are allotted. The communication terminal is configured to receive NTP packets from the allotted NTP servers 10 to acquire time.

Herein, in the first illustrative embodiment, a reference of "time" is Universal Time Coordinated (UTC) time. However, the reference of "time" is not limited to the UTC time and may be information indicative of standard time or any information which can be a reference of time. For example, the reference of "time" may be Greenwich Mean Time (GMT) time. In the first illustrative embodiment, "time" includes not only hour and minute but also date.

Figure 2:
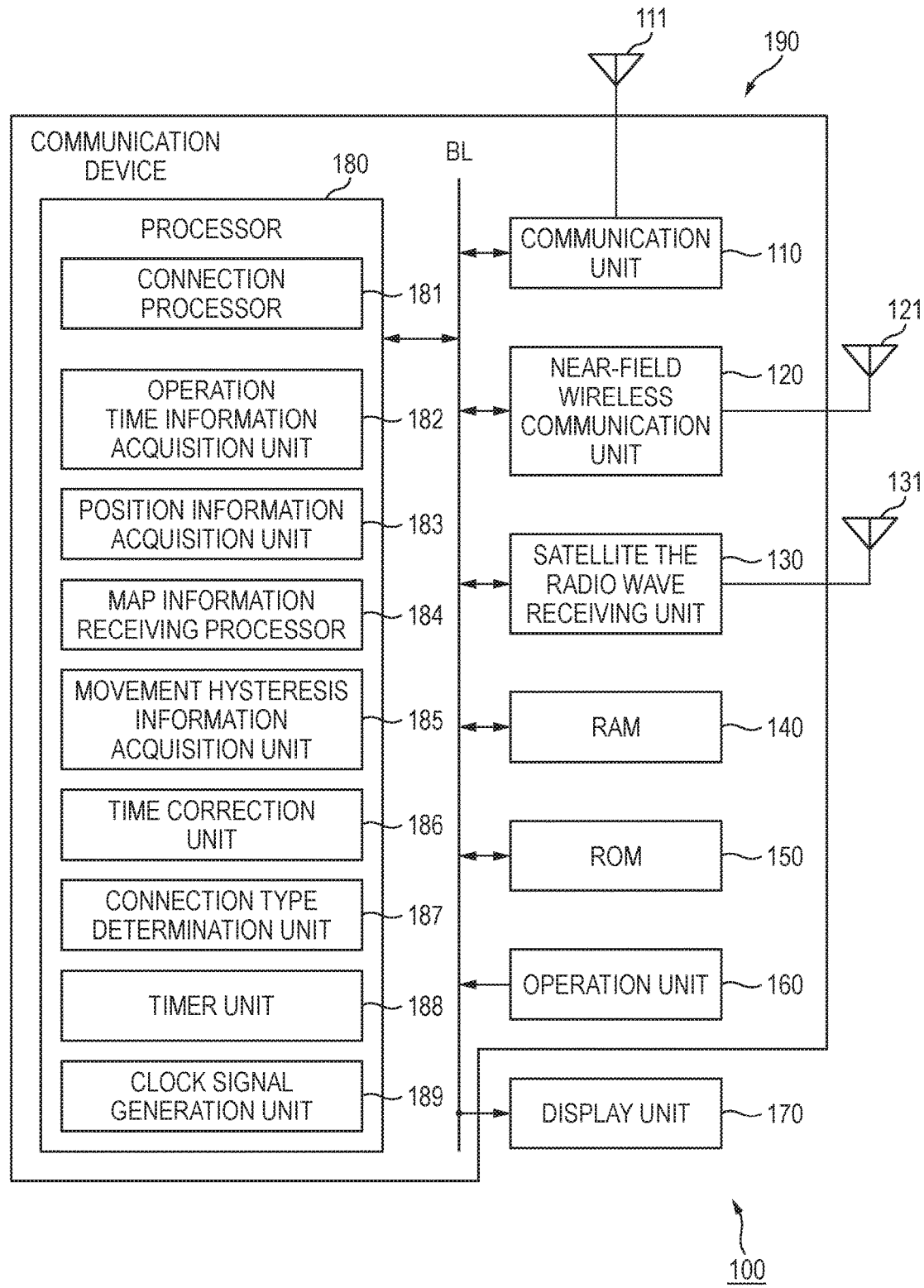
FIG. 2 is a block diagram illustrating an exemplary configuration of a smart phone according to the first illustrative embodiment.

Subsequently, a configuration of the smart phone 100 according to the first illustrative embodiment is described. As shown in FIG. 2, the smart phone 100 includes a communication device 190 and a display unit 170. The communication device 190 includes a communication unit 110 (a first receiver), a near-field wireless communication unit 120 (a second receiver), a satellite radio wave receiving unit 130 (a third receiver), a Random Access Memory (RAM) 140, a Read Only Memory (ROM) 150, an operation unit 160 and a processor 180. The constitutional elements of the communication device 190 and the display unit 170 are connected to each other via a bus line BL.

The communication unit 110 includes a Radio Frequency (RF) circuit, a Base Band (BB) circuit, an Large Scale Integration (LSI) and the like, for example. The communication unit 110 is configured to perform wireless communication with a relay device, an access point and the like via an antenna 111. The communication unit 110 is connected to the WAN 50 via the relay device, the access point and the like, and is configured to perform communication with the NTP servers 10, the NTP pool server 20, the location server 30 and the map information distribution server 60. In the meantime, the communication unit 110 may be connected to the WAN 50 and configured to perform communication with the other devices through wired communication, rather than the configuration of performing wireless communication with the relay device, the access point and the like via the antenna 111.

The near-field wireless communication unit 120 includes a radio frequency circuit, a base band circuit, an LSI and the like, for example. The near-field wireless communication unit 120 is configured to transmit and receive a signal via an antenna 121 and to perform wireless communication with the electronic timepiece 200, which is the other wireless communication device, based on the BLE.

The satellite radio wave receiving unit 130 includes a radio frequency circuit, a base band circuit, an LSI and the like, for example. The satellite radio wave receiving unit 130 is configured to receive a radio wave from the satellite 40 via an antenna 131.

The RAM 140 includes a volatile memory and is used as a work area for temporarily storing therein data so as for the processor 180 to execute a variety of processing.

The ROM 150 includes a non-volatile memory such as a flash memory and stores therein programs (for example, programs for implementing information acquisition processing, time correction processing and the like, which will be described later) by which the processor 180 is to control various functions, and various data (for example, data indicative of a restriction area A1, a determination target area A2, information acquired in information acquisition processing and the like, which will be described later).

The operation unit 160 includes an operation button, a touch panel and the like, and is an interface which is used for a user to input an instruction.

The display unit 170 includes a Liquid Crystal Display (LCD), an Electro Luminescence (EL) display or the like and is configured to display an image based on image data input from the processor 180.

The processor 180 includes a Central Processing Unit (CPU). The processor 180 is configured to control an entire operation of the smart phone 100 by executing various programs stored in the ROM 150.

Herein, a functional configuration of the processor 180 of the smart phone 100 is described.

The processor 180 is configured to function as a connection processor 181, an operation time information acquisition unit 182, a position information acquisition unit 183, a map information receiving processor 184, a movement history information acquisition unit 185, a time correction unit 186, a connection type determination unit 187, a timer unit 188, and a clock signal generation unit 189.

The connection processor 181 is configured to control connection with the electronic timepiece 200. This control includes connection establishment processing and disconnection processing.

In the connection establishment processing, the connection processor 181 is configured to control the near-field wireless communication unit 120 based on a scan instruction and to receive an advertisement which is transmitted from the electronic timepiece 200. The connection processor 181 having received the advertisement controls the near-field wireless communication unit 120 to transmit a signal indicative of a connection request to the electronic timepiece 200 when connection is required.

The advertisement is notification information by which the electronic timepiece 200 enables the smart phone 100 to recognize the electronic timepiece 200. A user operation for the scan instruction of the smart phone 100 may be, for example, activation of an application for using a service of the electronic timepiece 200. The scan instruction is not limited to the user operation and may be periodically made after the application is activated.

In the disconnection processing, the connection processor 181 is configured to control the near-field wireless communication unit 120 to transmit a disconnection request to the electronic timepiece 200 connected thereto. This processing is executed when data communication with the connected electronic timepiece 200 is over or when the user performs a disconnection operation, for example.

The operation time information acquisition unit 182 is configured to acquire operation time information, which indicates time at which the electronic timepiece 200 receives an information acquisition instruction by the proximity operation. Specifically, the operation time information acquisition unit 182 is configured to control the near-field wireless communication unit 120 to receive an acquisition instruction notification transmitted from the electronic timepiece 200. The operation time information acquisition unit 182 is configured to acquire, as the operation time information, time at which the acquisition instruction notification is received.

Strictly speaking, the operation time information is information indicative of time slightly later than time at which the electronic timepiece 200 receives an information acquisition instruction by the proximity operation. However, since a temporal difference therebetween is small, both are substantially the same.

The position information acquisition unit 183 is configured to acquire position information which indicates a user position at time based on the operation time information acquired by the operation time information acquisition unit 182.

Herein, the user position is described. The smart phone 100 is configured to perform near-field wireless communication with the electronic timepiece 200. The user performs proximity operation to the electronic timepiece 200. Considering this condition, it can be said that there is a close positional relation among the smart phone 100, the electronic timepiece 200 and the user.

For example, at the positional relation, even when a distance apart from each other is about 2 m, the distance can be ignored on a map. A position of the smart phone 100 is substantially the same as a position of the user. For this reason, in the first illustrative embodiment, a current position of the smart phone 100 is used as the user position.

There are two acquisition methods for acquiring the position information by the position information acquisition unit 183. In a first acquisition method, the position information acquisition unit 183 is configured to control the communication unit 110 to perform communication with the NTP pool server 20 and to receive an NTP packet from the NTP server 10 allotted by the NTP pool server 20. In this case, the position information acquisition unit 183 is configured to acquire, as the position information, a position (latitude and longitude) indicated by the received NTP packet.

In a second acquisition method, the position information acquisition unit 183 is configured to control the satellite radio wave receiving unit 130 to receive a radio wave from the satellite 40. In this case, the position information acquisition unit 183 is configured to calculate a position (latitude and longitude) based on the received radio wave and to acquire the position, as the position information.

In the meantime, in any acquisition method, the position information acquisition unit 183 is configured to rapidly acquire the position information after the operation time information acquisition unit 182 receives the acquisition instruction notification transmitted from the electronic timepiece 200. This is to reduce an error of the position information, which is caused due to a time difference from time at which the proximity operation is performed on the electronic timepiece 200 to acquisition time of the position information.

The map information receiving processor 184 is configured to control the communication unit 110 to receive map information, which indicates the position information acquired from the map information distribution server 60 by the position information acquisition unit 183. The map information is information for indicating the position information on a map.

In the meantime, some countries apply a restriction on acquiring and displaying the position information or acquiring and displaying the map information in some regions such that positions of important facilities of governments are not specified due to national security reasons. For example, in some cases, it may be illegal for a user to know a current position of the user by using the radio wave from the satellite, a network or the like at the periphery of the important facilities of governments.

In the below, a country which applies the restriction is referred to as "specific country". Herein, a relation between a restriction area A1 and a determination target area A2 of the first illustrative embodiment is described with reference to FIG. 4.

In the first illustrative embodiment, an area to which an address of the specific country is assigned, i.e., an area in the specific country is referred to as a restriction area A1. The restriction area A1 may be only some regions for which the specific country applies a restriction. In this case, however, since there are concerns that the communication terminal will display the position information and the map information in the restriction area A1 due to a response speed of the communication terminal, an error of the position information and the like, for example, it is necessary to secure measures to prevent the same.

Figure 4:
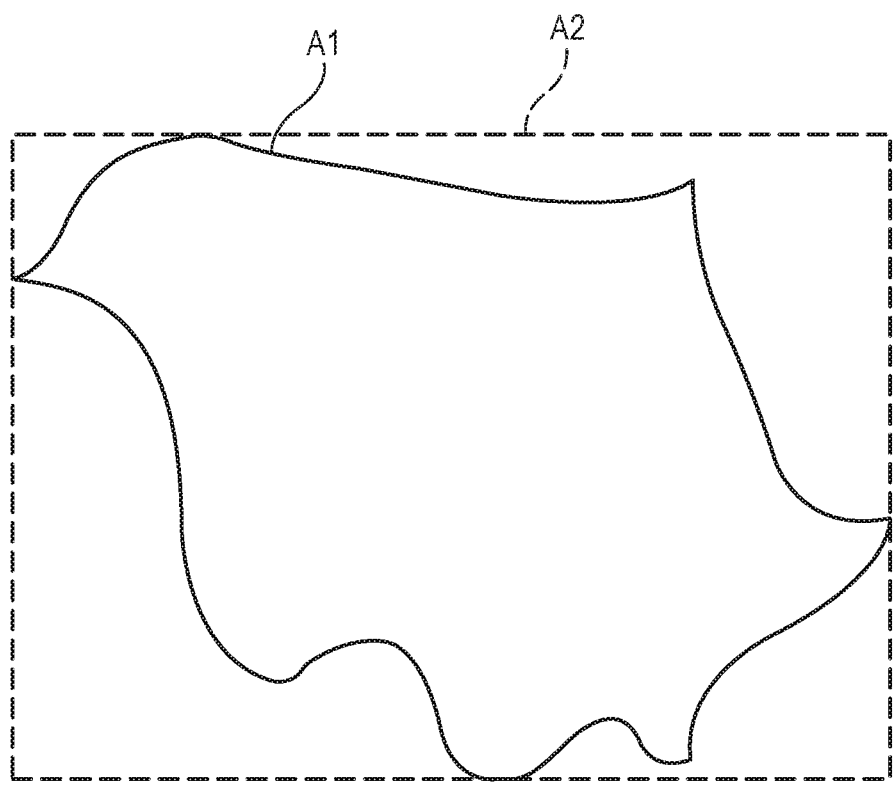
FIG. 4 is a conceptual view for illustrating a relation between a restriction area and a determination target area according to the first illustrative embodiment.

Herein, an area for which the processor 180 determines whether the acquired position information is within the restriction area A1 is referred to as a determination target area A2. As shown in FIG. 4, in the first illustrative embodiment, the determination target area A2 shown with the broken line is set as a rectangular shape in which the restriction area A1 shown with the solid line is inscribed. In the meantime, the determination target area A2 is not limited to the rectangular shape and may be an area having a range greater than the restriction area A1. Meanwhile, data indicative of a range of the latitude and longitude indicating the determination target area A2 and information indicative of the specific country, which is the restriction area A1, are stored in advance in the ROM 150 by a manufacturer, a vendor and the like, for example.

When the processor 180 determines that the acquired position information is outside the restriction area A1, the map information receiving processor 184 receives the map information from the map information distribution server 60.

The movement history information acquisition unit 185 is configured to acquire movement history information, based on the plurality of map information received by the map information receiving processor 184 and stored in the ROM 150. The movement history information is information indicative of a moving path formed by linearly connecting positions, which are indicated on a map by the plurality of map information, in a time-series order.

The time correction unit 186 is configured to acquire the UTC time and to correct time which is measured by the timer unit 188 (described later). The time correction unit 186 is configured to control the near-field wireless communication unit 120 to transmit time measured by the timer unit 188 to the electronic timepiece 200. As described later, the electronic timepiece 200 is configured to correct time based on the received time.

As the acquisition method of the UTC time by the time correction unit 186, there are two acquisition methods. In a first acquisition method, the time correction unit 186 is configured to control the communication unit 110 to perform communication with the NTP pool server 20 and to receive an NTP packet from the NTP server 10 allotted by the NTP pool server 20. The time correction unit 186 is configured to acquire time information included in the NTP packet, as the UTC time.

In a second acquisition method, the time correction unit 186 is configured to control the satellite radio wave receiving unit 130 to receive a radio wave from the satellite 40. The time correction unit 186 is configured to acquire time information generated from the radio wave received from the satellite 40, as the UTC time.

In the meantime, the time correction processing which is executed by the time correction unit 186 may be executed periodically (for example, every 30 minutes) or at timing based on a user operation.

The connection type determination unit 187 is configured to determine what purpose a connection type received from the electronic timepiece 200 indicates. The processor 180 is configured to execute control processing thereafter, in correspondence to a determination result thereof. For example, when a purposed indicated by the connection type includes the time correction processing, the connection type determination unit 187 transmits time measured by the timer unit 188 to the electronic timepiece 200. The purpose indicated by the connection type includes not only the time correction processing but also a purpose for searching the smart phone 100 and a purpose for performing various data communications.

The timer unit 188 is configured to count a number of pulses of a clock signal, which is generated by the clock signal generation unit 189 and to measure time based on the number of pulses to be counted. The processor 180 is configured to execute various controls at timing based on the number of pulses counted by the timer unit 188.

The clock signal generation unit 189 is configured to generate a clock signal of the own device (the smart phone 100). In the meantime, when performing clock synchronization in correspondence to a signal received from the other device, the processor 180 appropriately controls a frequency of the clock signal of the clock signal generation unit 189.

In the above, the configuration of the smart phone 100 according to the first illustrative embodiment has been described. Next, a configuration of the electronic timepiece 200 according to the first illustrative embodiment is described.

Figure 3:
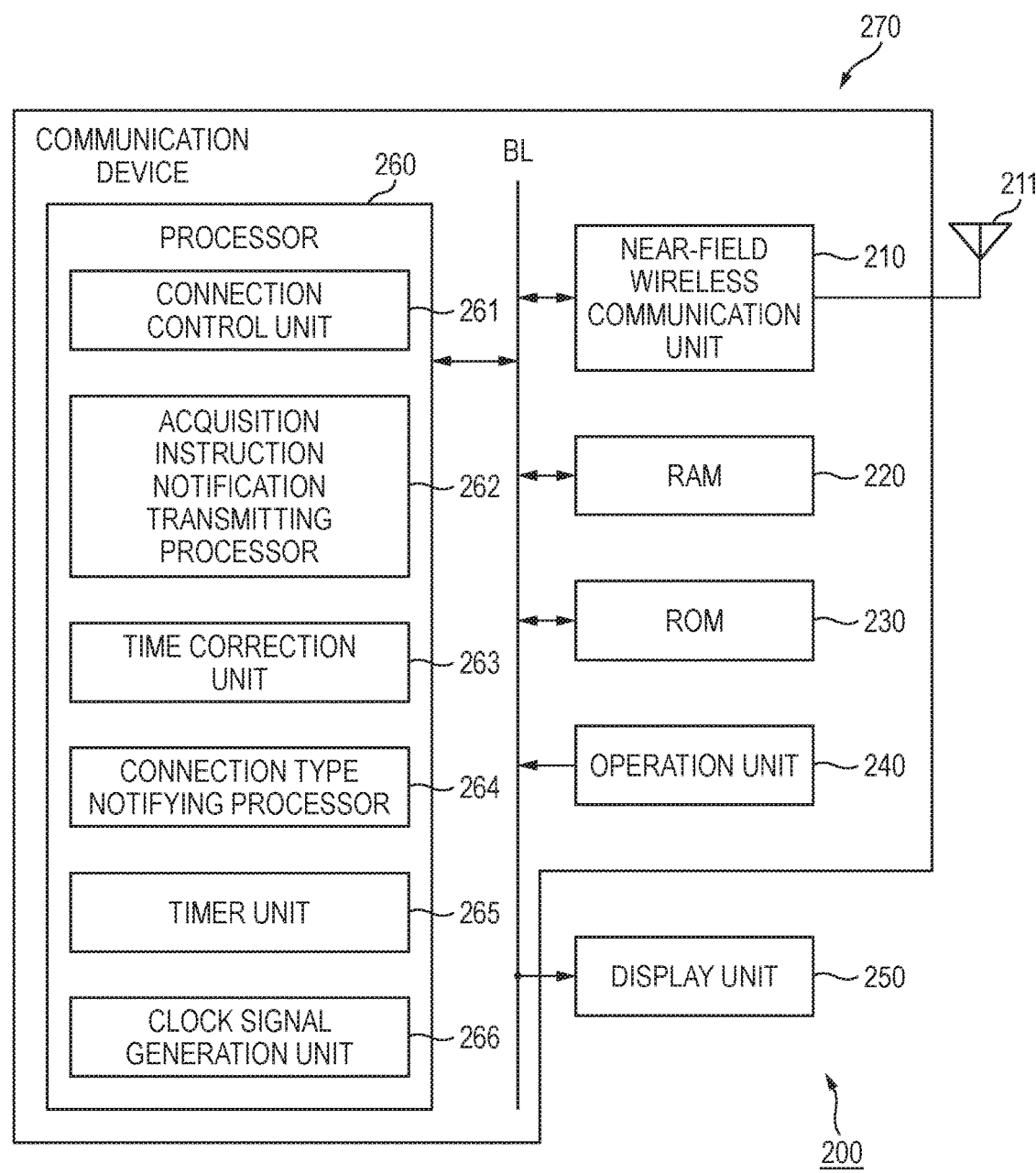
FIG. 3 is a block diagram illustrating an exemplary configuration of an electronic timepiece according to the first illustrative embodiment.

As shown in FIG. 3, the electronic timepiece 200 includes a communication device 270 and a display unit 250. The communication device 270 includes a near-field wireless communication unit 210, a RAM 220, a ROM 230, an operation unit 240 and a processor 260. The constitutional elements of the communication device 270 and the display unit 250 are connected to each other via a bus line BL.

The near-field wireless communication unit 210 includes an RF circuit, a BB circuit, an LSI and the like, for example. The near-field wireless communication unit 210 is configured to perform wireless communication with the smart phone 100, which is the other wireless communication device, via an antenna 211, based on the BLE.

The RAM 220 includes a volatile memory and is used as a work area for temporarily storing therein data so as for the processor 260 to execute a variety of processing.

The ROM 230 includes a non-volatile memory such as a flash memory and stores therein programs (for example, programs for implementing time correction processing, information acquisition processing and the like, which will be described later) by which the processor 260 is to control diverse functions, and various data.

The operation unit 240 includes an operation button, a touch panel and the like, and is an interface for receiving a user's operation. The operation unit 240 is configured to receive a proximity operation, which is not a remote operation by an external device but a physical operation such as a pushing operation on the operation button and a touch operation on the touch panel.

The display unit 250 includes an LCD, an EL display or the like and is configured to display an image based on image data input from the processor 260.

The processor 260 is a processor and includes a CPU. The processor 260 is configured to control an entire operation of the electronic timepiece 200 by executing various programs stored in the ROM 230.

Herein, a functional configuration of the processor 260 of the electronic timepiece 200 is described. The processor 260 is configured to function as a connection processor 261, an acquisition instruction notification transmitting processor 262, a time correction unit 263, a connection type notifying processor 264, a timer unit 265, and a clock signal generation unit 266.

The connection processor 261 is configured to control connection with the smart phone 100. This control includes connection establishment processing and disconnection processing.

In the connection establishment processing, the connection processor 261 is configured to control the near-field wireless communication unit 210 to transmit an advertisement to the smart phone 100. The transmission of the advertisement is performed at periodic timing in correspondence to processing of the program, or at timing at which a user operation is performed.

After transmitting the advertisement, the connection processor 261 is configured to receive a signal indicative of a connection request from the smart phone 100 via the near-field wireless communication unit 210 and to establish connection with the smart phone 100. Once the connection is established, data communication with the smart phone 100 becomes available.

In the disconnection processing, the connection processor 261 is configured to receive a signal indicative of a disconnection request from the smart phone 100 via the near-field wireless communication unit 210 and to disconnect the connection with the smart phone 100.

When the user pushes an operation button for executing an information acquisition instruction on the operation unit 240, the acquisition instruction notification transmitting processor 262 controls the near-field wireless communication unit 210 to transmit an acquisition instruction notification to the smart phone 100. The information acquisition instruction is an instruction by which the user instructs the electronic timepiece 200 to transmit the acquisition instruction notification. The acquisition instruction notification is a notification for instructing the smart phone 100 to acquire the operation time information.

The time correction unit 263 is configured to receive time transmitted from the smart phone 100, via the near-field wireless communication unit 210, in time correction processing. The time correction unit 263 is configured to correct time, which is measured by the timer unit 265, based on the received time. Accordingly, the electronic timepiece 200 keeps a time-synchronized state with the smart phone 100.

The connection type notifying processor 264 is configured to control the near-field wireless communication unit 210 to notify a connection type to the smart phone 100.

Herein, the connection type is information indicative of a purpose of the electronic timepiece 200 to connect to the smart phone 100. The connection type is determined by a content of a user operation to the electronic timepiece 200.

The timer unit 265 is configured to count a number of pulses of a clock signal, which is generated by the clock signal generation unit 266 and to measure time based on the number of pulses to be counted. The processor 260 is configured to execute various controls at timing based on the number of pulses counted by the timer unit 265.

The clock signal generation unit 266 is configured to generate a clock signal of the own device (the electronic timepiece 200). In the meantime, when performing clock synchronization in correspondence to a signal received from the other device, the processor 260 appropriately controls a frequency of the clock signal of the clock signal generation unit 266.

Figure 5:
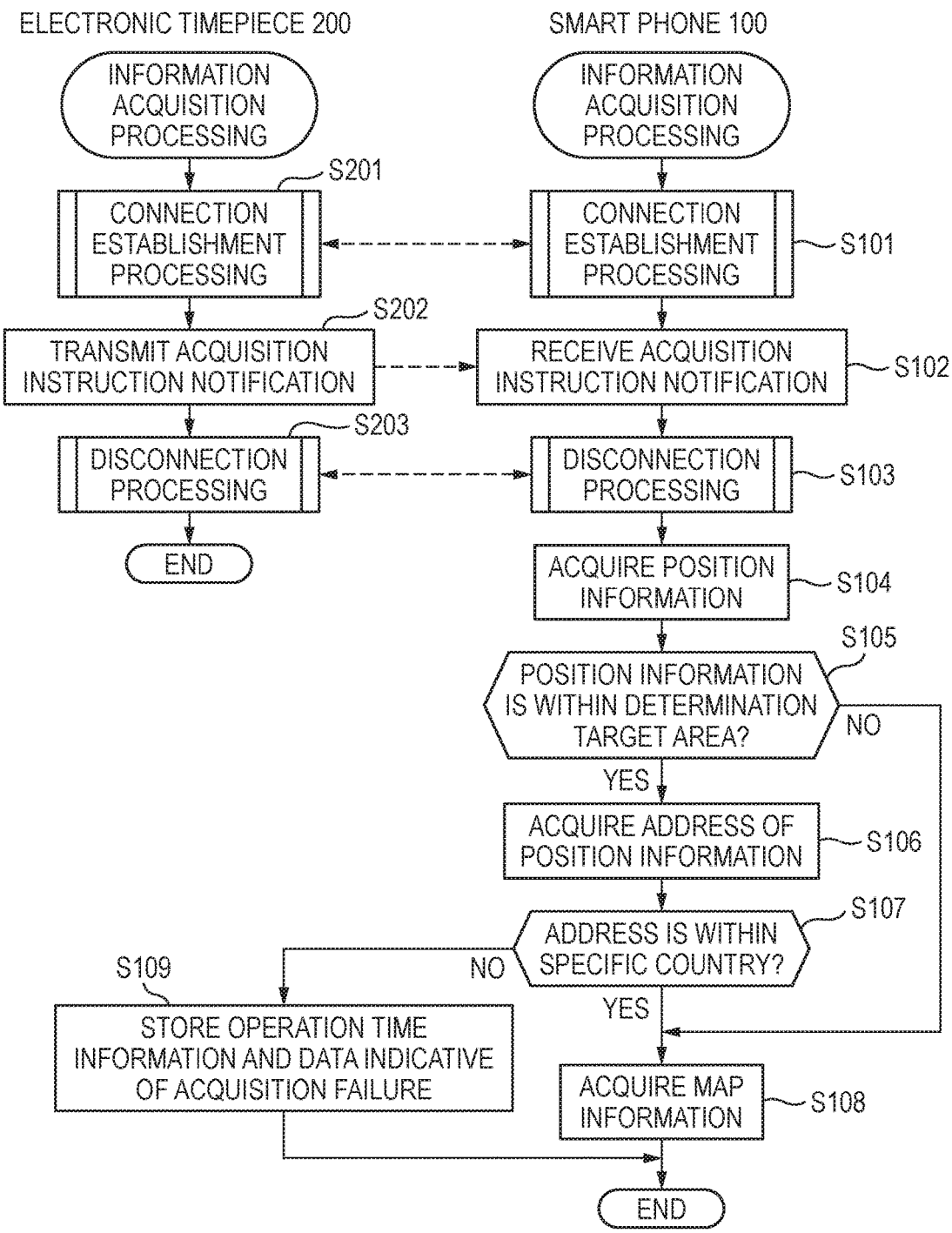
FIG. 5 is a flowchart illustrating an example of information acquisition processing which is executed by the smart phone and the electronic timepiece according to the first illustrative embodiment.

In the above, the configuration of the electronic timepiece 200 according to the first illustrative embodiment has been described. Next, an example of information acquisition processing which is executed by the smart phone 100 and the electronic timepiece 200 is described with reference to FIG. 5.

The information acquisition processing is executed when the operation button for executing the information acquisition instruction is pushed on the operation unit 240 of the electronic timepiece 200.

When the information acquisition processing is executed, connection establishment processing for establishing connection between the electronic timepiece 200 and the smart phone 100 is executed (steps S201 and S101). Specifically, the connection processor 261 of the electronic timepiece 200 transmits an advertisement to the smart phone 100, and the connection processor 181 of the smart phone 100 transmits a signal indicative of a connection request to the electronic timepiece 200, as a reply. The connection processor 261 of the electronic timepiece 200 receives the signal indicative of a connection request and establishes connection.

When the connection between the electronic timepiece 200 and the smart phone 100 is established, the acquisition instruction notification transmitting processor 262 of the electronic timepiece 200 transmits the acquisition instruction notification to the smart phone 100 (step S202). The operation time information acquisition unit 182 of the smart phone 100 receives the acquisition instruction notification transmitted from the electronic timepiece 200 (step S102). The operation time information acquisition unit 182 of the smart phone 100 acquires time at which the acquisition instruction notification is received, as the operation time information.

Herein, disconnection processing of disconnecting the connection between the electronic timepiece 200 and the smart phone 100 is executed (steps S203 and S103). Specifically, the connection processor 181 of the smart phone 100 transmits a signal indicative of a disconnection request to the connected electronic timepiece 200, and the connection processor 261 of the electronic timepiece 200 disconnects the connection with the smart phone 100.

The position information acquisition unit 183 of the smart phone 100 acquires a current position of the smart phone 100, as the position information indicative of the user position (step S104). The position information acquisition unit 183 of the smart phone 100 may acquire the position information from the NTP packet received via the communication unit 110, or may acquire the position information based on the radio wave received from the satellite 40 via the satellite radio wave receiving unit 130.

Herein, the processor 180 of the smart phone 100 refers to the ROM 150 and determines whether the acquired position information is within the determination target area A2 (step S105).

When the processor 180 of the smart phone 100 determines that the acquired position information is not within the determination area A2 (step S105; No), steps S106 and S107, which will be described later, are skipped, and the processor 180 proceeds to step S108, which will be described later.

On the other hand, when the processor 180 of the smart phone 100 determines that the acquired position information is within the determination area A2 (step S105; Yes), the processor 180 of the smart phone 100 acquires an address of the position information (step S106). Specifically, the processor 180 of the smart phone 100 controls the communication unit 110 to transmit the latitude and longitude of the position information to the map information distribution server 60. The processor 180 of the smart phone 100 receives an address corresponding to the latitude and longitude of the position information via the communication unit 110.

The processor 180 of the smart phone 100 determines whether the acquired address is an address outside the specific country (step S107). This determination is performed by referring to the information indicating the specific country and stored in the ROM 150 by the processor 180 of the smart phone 100.

When the processor 180 of the smart phone 100 determines that the acquired address is an address outside the specific country (step S107; Yes), the map information receiving processor 184 of the smart phone 100 receives and acquires map information corresponding to the position information from the map information distribution server 60 via the communication unit 110 (step S108). In this case, the processor 180 of the smart phone 100 stores the map information acquired by the map information receiving processor 184 in the ROM 150 in association with the time indicated by the operation time information acquired by the operation time information acquisition unit 182.

On the other hand, when the processor 180 of the smart phone 100 determines that the acquired address is inside the specific country (step S107; No), the processor 180 of the smart phone 100 stores the operation time information acquired by the operation time information acquisition unit 182 and data, which indicates that the map information is an acquisition failure, in the ROM 150 (step S109). In the meantime, the processor 180 of the smart phone 100 displays the information stored in the ROM 150 on the display unit 170 in response to the user operation.

In the above, the example of the information acquisition processing which is executed by the smart phone 100 and the electronic timepiece 200 has been described. The information acquisition processing is executed each time when the operation button for executing the information acquisition instruction is pushed on the operation unit 240 of the electronic timepiece 200. Therefore, the map information is accumulated in the ROM 150.

Herein, when the user performs an operation for acquiring the movement history information on the operation unit 160 of the smart phone 100, the movement history information acquisition unit 185 of the smart phone 100 reads out the plurality of map information stored in the ROM 150 in a time-series manner based on the times indicated by the operation time information and transmits the same to the map information distribution server 60. The movement history information acquisition unit 185 of the smart phone 100 acquires the movement history information by causing the map information distribution server 60 to generate the movement history information and receiving the same.

Herein, examples of an image displayed as the map information and an image displayed as the movement history information on the display unit 170 of the smart phone 100 are described. Herein, a case where the acquired map information is three map information shown in FIGS. 6A, 6B and 6C is described.

Figure 6A:
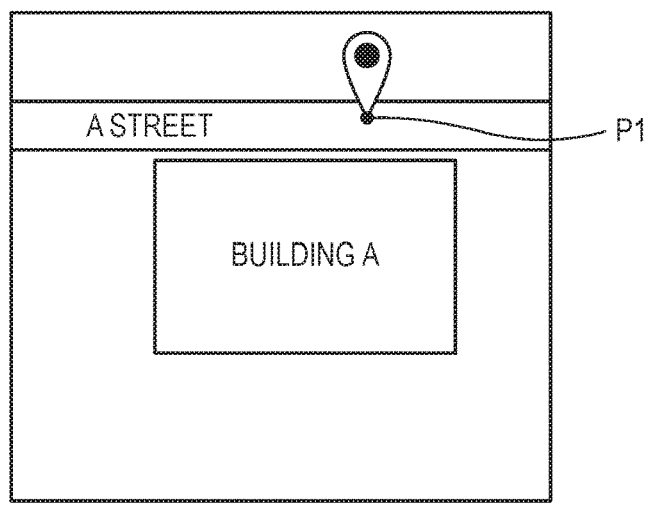
FIG. 6A illustrates an example of an image which is displayed as map information by the smart phone according to the first illustrative embodiment.
Figure 6B:
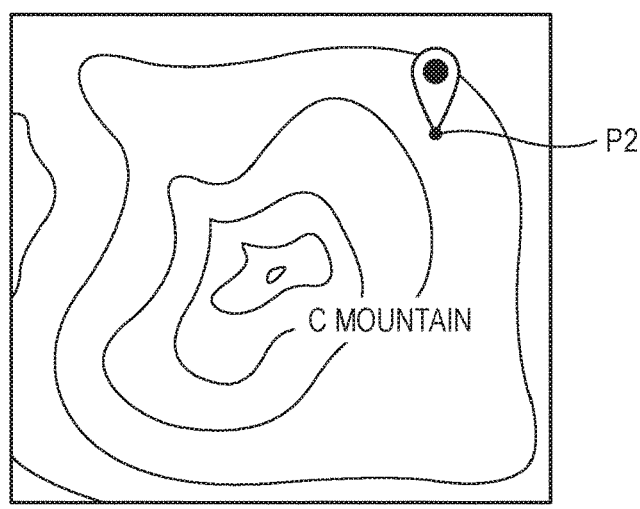
FIG. 6B illustrates an example of an image which is displayed as the map information by the smart phone according to the first illustrative embodiment.
Figure 6C:
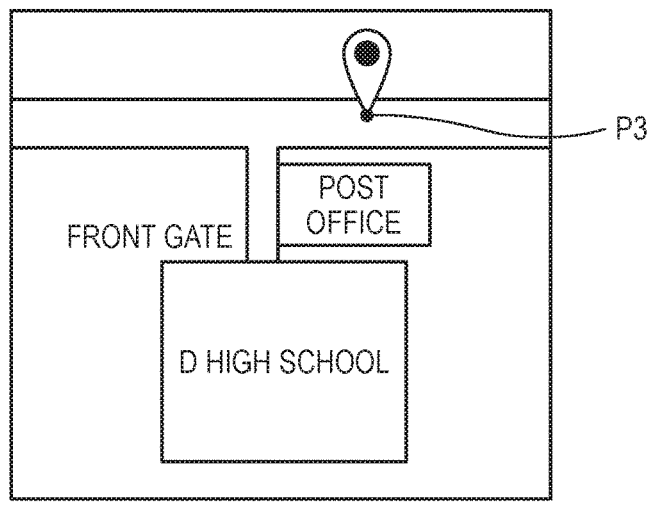
FIG. 6C illustrates an example of an image which is displayed as the map information by the smart phone according to the first illustrative embodiment.

FIG. 6A illustrates first map information and shows a point P1 as first acquired position information on a map. FIG. 6B illustrates second map information and shows a point P2 as secondarily acquired position information on the map. FIG. 6C illustrates third map information and shows a point P3 as thirdly acquired position information on the map.

Figure 7:
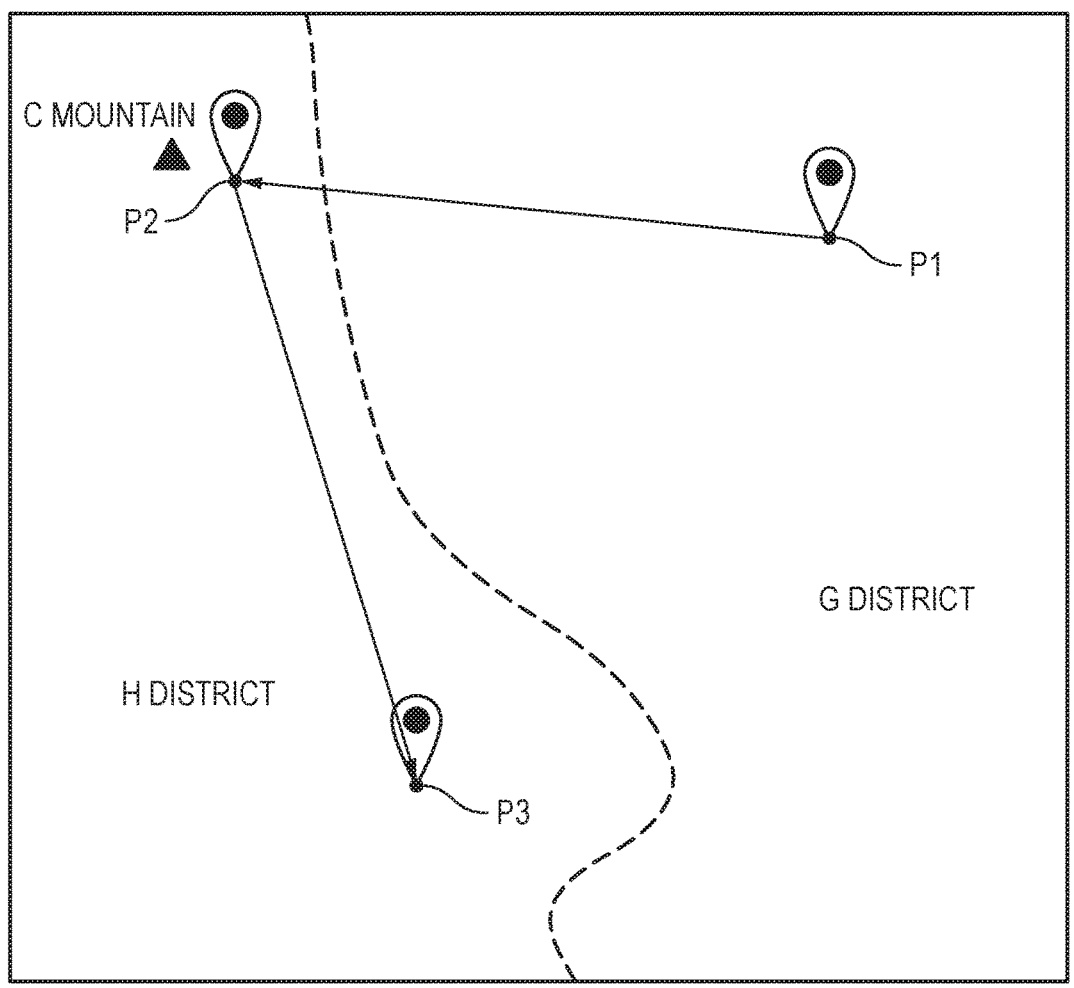
FIG. 7 is a view illustrating an example of an image which is displayed as movement history information by the smart phone according to the first illustrative embodiment.

In this case, as shown in FIG. 7, in an image displayed as the movement history information, the points P1, P2, P3 are linearly connected in order of acquired times on a map of a scale in which the points P1, P2, P3 are all displayed. This movement history information is generated by cooperation between the movement history information acquisition unit 185 of the smart phone 100 and the map information distribution server 60.

As described above, in the communication system 1 according to the first illustrative embodiment, when the operation button of the electronic timepiece 200 for executing the information acquisition instruction is pushed, the smart phone 100 acquires the map information for indicating the position information at that time on the map. In this case, the user can acquire the map information simply by pushing the operation button of the electronic timepiece 200.

Therefore, according to the communication system 1 of the first illustrative embodiment, the operability for acquiring the map information indicative of the position information on the map can be improved. In particular, since the operation of pushing the operation button of the electronic timepiece 200 is an operation which can be performed in a short time, the map information can be acquired at user's intended timing.

Also, the acquired plurality of map information are respectively stored with being associated with the operation time information in the ROM 150. Therefore, the movement history information can be acquired from the acquired plurality of map information. Particularly, even when the user is moving, the movement history information is quickly generated at user's intended timing based on the acquired position information. Therefore, an error can be reduced that the position information is incorrect due to the delay associated with the operation time.

The map information is acquired only when the position information is outside the restriction area A1 to which the address of the specific country is assigned. The map information and the position information are displayed on the display unit 170 of the smart phone 100 only when the position information is outside the restriction area A1 to which the address of the specific country is assigned. Therefore, the user can use the communication system 1 without concerns about the restrictions on the acquisition, display and the like of the map information and the position information in the specific country. Accordingly, the convenience is improved.

Also, the processing of determining whether the position information is outside the restriction area A1 is executed only when the position information is within the determination target area A2 which is a peripheral area of the restriction area A1. Therefore, an amount of communication processing can be suppressed as compared to a configuration where the determination processing is always performed.

(Second Illustrative Embodiment)

A communication system according to the second illustrative embodiment includes a smart phone 300 which is a wireless communication device, and an electronic timepiece 400 which is a wireless communication device different from the smart phone 300.

The communication system according to the second illustrative embodiment is used in the substantially similar manner to the first illustrative embodiment. In the using manner of the communication system according to the second illustrative embodiment, the smart phone 100 of FIG. 1 is changed to the smart phone 300, and the electronic timepiece 200 is changed to the electronic timepiece 400. The others are the same as the first illustrative embodiment. In below descriptions, the constitutional elements common to those of the first illustrative embodiment are denoted with the same reference numerals.

Figure 8:
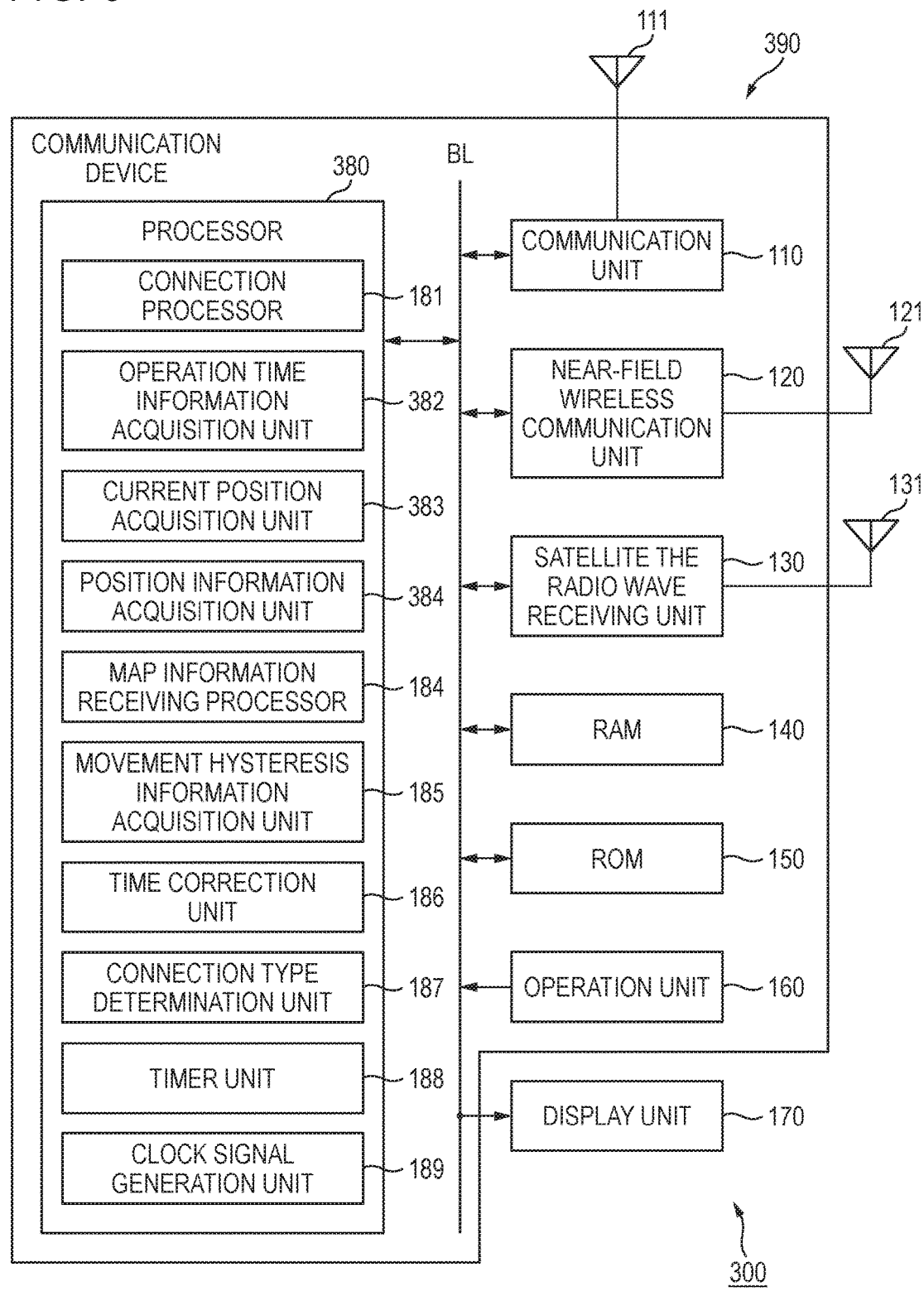
FIG. 8 is a block diagram illustrating an exemplary configuration of a smart phone according to a second illustrative embodiment.

In the below, the smart phone 300 according to the second illustrative embodiment is described. As shown in FIG. 8, the smart phone 300 includes a communication device 390 and the display unit 170. The communication device 390 includes the communication unit 110, the near-field wireless communication unit 120, the satellite radio wave receiving unit 130, the RAM 140, the ROM 150, the operation unit 160 and a processor 380. The constitutional elements of the communication device 390 and the display unit 170 are connected to each other via the bus line BL.

The smart phone 300 is different from the smart phone 100 of the first illustrative embodiment in that it includes the processor 380, instead of the processor 180. The other configurations are the same as the smart phone 100. Further, in the second illustrative embodiment, the ROM 150 does not store therein the data indicative of the restriction area A1 and the determination target area A2. Instead, in the second illustrative embodiment, the ROM 150 stores therein a program for implementing point list generation processing, which will be described later, and a point list.

The processor 380 is a processor and includes a CPU. The processor 380 is configured to control an entire operation of the smart phone 300 by executing various programs stored in the ROM 150. In the below, a functional configuration of the processor 380 of the smart phone 300 is described.

The processor 380 is configured to function as the connection processor 181, an operation time information acquisition unit 382, a current position information acquisition unit 383, a position information acquisition unit 384, the map information receiving processor 184, the movement history information acquisition unit 185, the time correction unit 186, the connection type determination unit 187, the timer unit 188, and the clock signal generation unit 189.

The operation time information acquisition unit 382 is configured to acquire operation time information transmitted from the electronic timepiece 400. Specifically, the operation time information acquisition unit 382 is configured to control the near-field wireless communication unit 120 to receive operation time information transmitted from the electronic timepiece 400. As described later, the operation time information is information indicative of time at which the information acquisition instruction by the proximate operation is received and which is stored in the ROM 230 by the electronic timepiece 400.

The current position acquisition unit 383 is configured to periodically acquire a current position of the smart phone 300. The current position acquired by the current position acquisition unit 383 is stored with being associated with acquisition time thereof in the ROM 150, as a point list. The point list is data in which the current position acquired by the smart phone 300 is stored to be readable in a time-series manner.

There are two acquisition methods for acquiring the current position by the current position acquisition unit 383. In a first acquisition method, the current position acquisition unit 383 is configured to control the communication unit 110 to perform communication with the NTP pool server 20 and to receive the NTP packet from the NTP server 10 allotted by the NTP pool server 20. In this case, the current position acquisition unit 383 is configured to acquire a position (latitude and longitude) indicated by the received NTP packet, as the current position.

In a second acquisition method, the current position acquisition unit 383 is configured to control the satellite radio wave receiving unit 130 to receive the radio wave from the satellite 40. In this case, the current position acquisition unit 383 is configured to calculate a position (latitude and longitude) based on the received radio wave and to acquire the position, as the current position.

The position information acquisition unit 384 is configured to acquire the position information indicative of a position at time based on the operation time information acquired by the operation time information acquisition unit 382.

Specifically, the position information acquisition unit 384 is configured to refer to the point list stored in the ROM 150 and to acquire, as the position information, a current position associated with the acquisition time, which is closest to the time indicated by the operation time information, of the plurality of current positions included in the point list.

In the above, the configuration of the smart phone 300 according to the second illustrative embodiment has been described. Next, a configuration of the electronic timepiece 400 according to the second illustrative embodiment is described.

Figure 9:
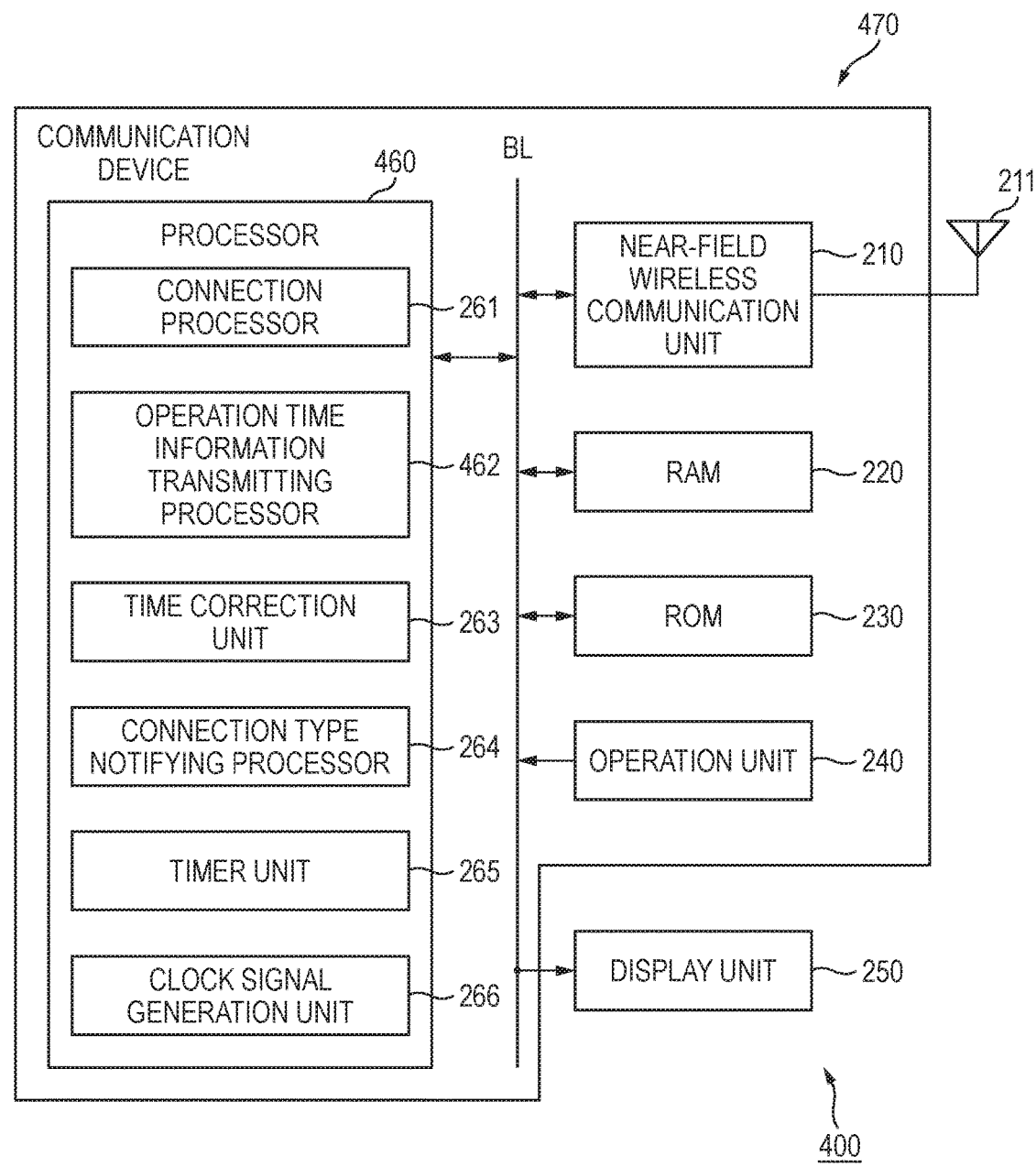
FIG. 9 is a block diagram illustrating an exemplary configuration of an electronic timepiece according to the second illustrative embodiment.

As shown in FIG. 9, the electronic timepiece 400 includes a communication device 470 and the display unit 250. The communication device 470 includes the near-field wireless communication unit 210, the RAM 220, the ROM 230, the operation unit 240 and a processor 460. The constitutional elements of the communication device 470 and the display unit 250 are connected to each other via the bus line BL.

The electronic timepiece 400 is different from the electronic timepiece 200 of the first illustrative embodiment in that it includes the processor 460, instead of the processor 260. The other configurations are the same as the electronic timepiece 200.

In the second illustrative embodiment, as described later, the ROM 230 also stores the operation time information which indicates time at which a pushing operation is received, each time when the user pushes the operation button for executing the information acquisition instruction on the operation unit 240 of the electronic timepiece 400. Therefore, when the operation button for executing the information acquisition instruction is repetitively pushed, the plurality of operation time information are accumulated in the ROM 230.

The processor 460 is a processor and includes a CPU. The processor 460 is configured to control an entire operation of the electronic timepiece 400 by executing various programs stored in the ROM 230.

Herein, a functional configuration of the processor 460 of the electronic timepiece 400 is described. The processor 460 is configured to function as the connection processor 261, an operation time information transmitting processor 462, the time correction unit 263, the connection type notifying processor 264, the timer unit 265 and the clock signal generation unit 266.

When the user executes an operation for transmitting the operation time information on the operation unit 240, the operation time information transmitting processor 462 controls the near-field wireless communication unit 210 to transmit the operation time information stored in the ROM 230 to the smart phone 300.

In the above, the configuration of the electronic timepiece 400 according to the second illustrative embodiment has been described. Next, an example of point list generation processing which is executed by the smart phone 300 is described with reference to FIG. 10. This processing is periodically and repetitively executed by the processor 380 of the smart phone 300.

First, when the point list generation processing is executed, the current position acquisition unit 383 of the smart phone 300 acquires a current position of the smart phone 300 (step S301). The current position acquisition unit 383 may acquire the current position from the NTP packet received via the communication unit 110, or may acquire the current position based on the radio wave received from the satellite 40 via the satellite radio wave receiving unit 130.

The current position acquisition unit 383 stores the acquired current position in association with the acquisition time thereof (step S302). Specifically, the current position acquisition unit 383 updates the point list stored in the ROM 150 by adding the acquired current position and the acquisition time thereof to the point list.

In the above, the example of the point list generation processing which is executed by the smart phone 300 has been described. Since the point list generation processing is periodically and repetitively executed, the acquired current position and the acquisition time thereof are accumulated in the point list of the ROM 150 over time.

Figure 10:
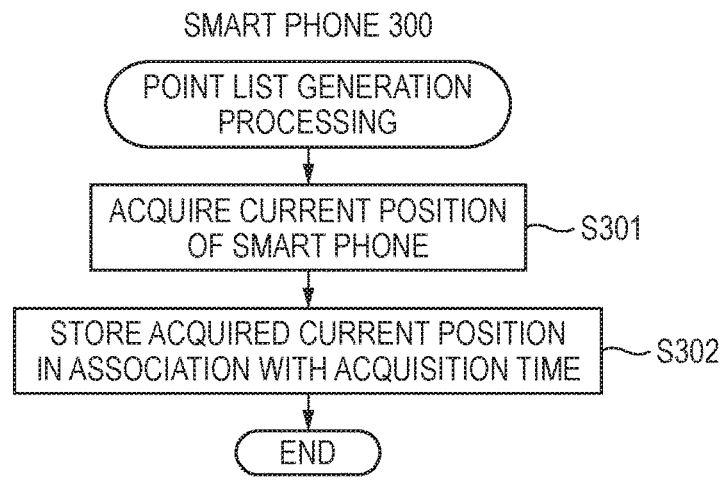
FIG. 10 is a flowchart illustrating an example of point list generation processing which is executed by the smart phone according to the second illustrative embodiment.
Figure 11:
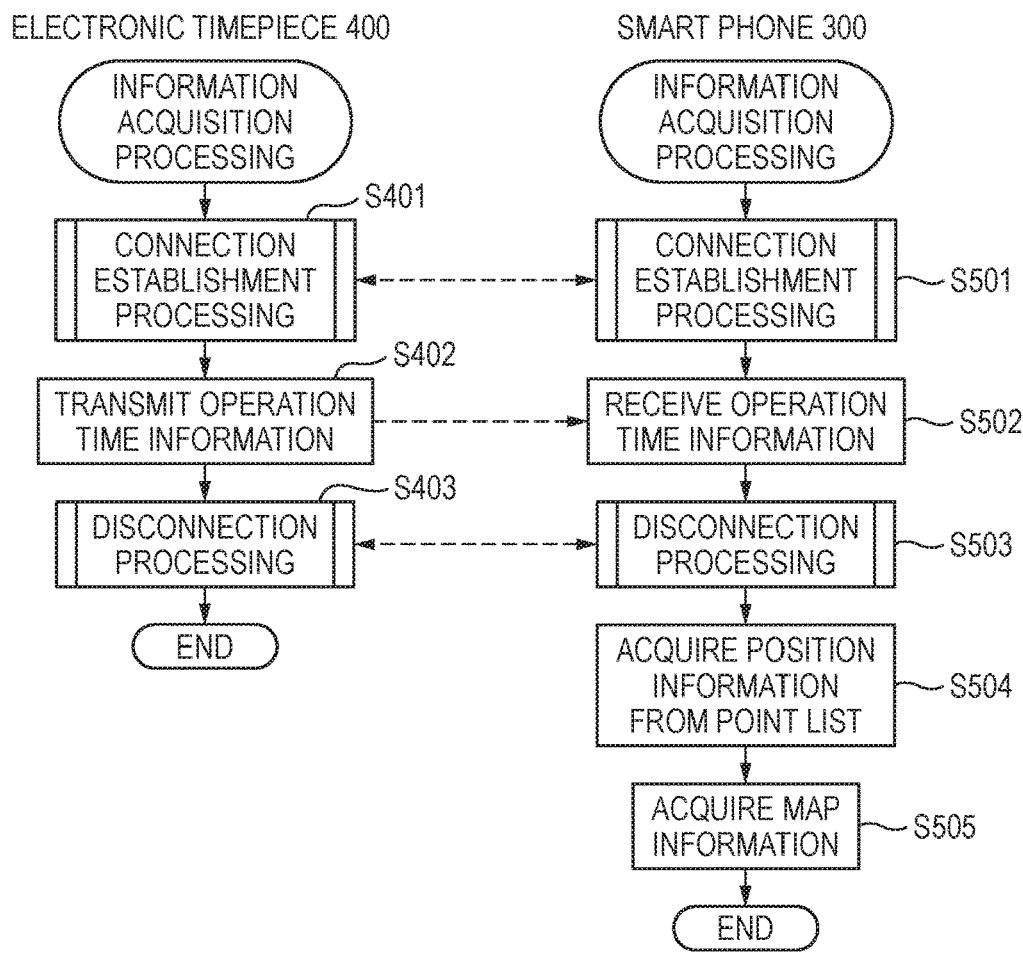
FIG. 11 is a flowchart illustrating an example of information acquisition processing which is executed by the smart phone and the electronic timepiece according to the second illustrative embodiment.

In the below, an example of information acquisition processing which is executed by the smart phone 300 and the electronic timepiece 400 is described with reference to FIG. 10. The information acquisition processing is executed when the user performs an operation for transmitting the operation time information stored in the ROM 230 of the electronic timepiece 400 to the smart phone 300 on the operation unit 240 of the electronic timepiece 400. The information acquisition processing may be periodically executed by the processor 460 of the electronic timepiece 400.

When the information acquisition processing is executed, connection establishment processing of establishing connection between the electronic timepiece 400 and the smart phone 300 is first executed (steps S401 and S501). This connection establishment processing is the same as the first illustrative embodiment.

When the connection between the electronic timepiece 400 and the smart phone 300 is established, the operation time information transmitting processor 462 of the electronic timepiece 400 transmits the operation time information stored in the ROM 230 to the smart phone 300 via the near-field wireless communication unit 210 (step S402). When a plurality of the operation time information are stored in the ROM 230, they are all transmitted. The operation time information transmitting processor 462 of the electronic timepiece 400 deletes the transmitted operation time information from the operation time information stored in the ROM 230.

The operation time information acquisition unit 382 of the smart phone 300 receives the operation time information transmitted from the electronic timepiece 400, via the near-field wireless communication unit 120 (step S502). Thereby, the operation time information acquisition unit 382 of the smart phone 300 receives the operation time information.

Herein, disconnection processing of disconnecting the connection between the electronic timepiece 400 and the smart phone 300 is executed (steps S403 and S503). This disconnection processing is the same as the first illustrative embodiment.

The position information acquisition unit 384 of the smart phone 300 acquires, as the position information, a current position associated with the acquisition time, which is closest to the time indicated by the operation time information received from the electronic timepiece 400, from the point list stored in the ROM 150 (step S504). When the plurality of operation time information are received from the electronic timepiece 400, the position information acquisition unit 384 acquires the plurality of position information corresponding to the plurality of operation time information.

Subsequently, the map information receiving processor 184 of the smart phone 300 receives and acquires the map information corresponding to the position information acquired by the position information acquisition unit 384, from the map information distribution server 60, via the communication unit 110 (step S505). When the position information acquisition unit 384 acquires the plurality of position information, the map information receiving processor 184 acquires the plurality of map information corresponding to the plurality of position information.

The processor 380 of the smart phone 300 stores the map information acquired by the map information receiving processor 184, in the ROM 150 in association with the time indicated by the operation time information acquired by the operation time information acquisition unit 382. The movement history information acquisition unit 185 of the smart phone 300 acquires the movement history information based on the plurality of map information stored in the ROM 150, similarly to the first illustrative embodiment.

As described above, in the second illustrative embodiment, the electronic timepiece 400 stores the time at which the operation button for executing the information acquisition instruction is pushed, in the ROM 230, as the operation time information. When the connection cannot be established between the electronic timepiece 400 and the smart phone 300, the electronic timepiece 400 cannot transmit the operation time information to the smart phone 300. However, after becoming a state where the connection can be established, the electronic timepiece 400 can transmit the operation time information stored in the ROM 230 to the smart phone 300.

In the second illustrative embodiment, the operation time information indicates the time at which the operation button for executing the information acquisition instruction is pushed on the operation unit 240 of the electronic timepiece 400. The smart phone 300 acquires, as the position information, the current position of the smart phone 300 associated with the acquisition time, which is closest to the time indicated by the operation time information, from the point list. Accordingly, the position information and the map information can be acquired at timing close to the time at which the operation button for executing the information acquisition instruction is pushed on the operation unit 240 of the electronic timepiece 400.

(Third Illustrative Embodiment)

A communication system according to the third illustrative embodiment includes a smart phone 500 which is a wireless communication device, and an electronic timepiece 600 which is a wireless communication device different from the smart phone 500.

The communication system according to the third illustrative embodiment is used in the substantially similar manner to the first illustrative embodiment. In the using manner of the communication system according to the third illustrative embodiment, the smart phone 100 of FIG. 1 is changed to the smart phone 500, and the electronic timepiece 200 is changed to the electronic timepiece 600. The others are the same as the first illustrative embodiment. In below descriptions, the constitutional elements common to those of the first illustrative embodiment are denoted with the same reference numerals.

Figure 12:
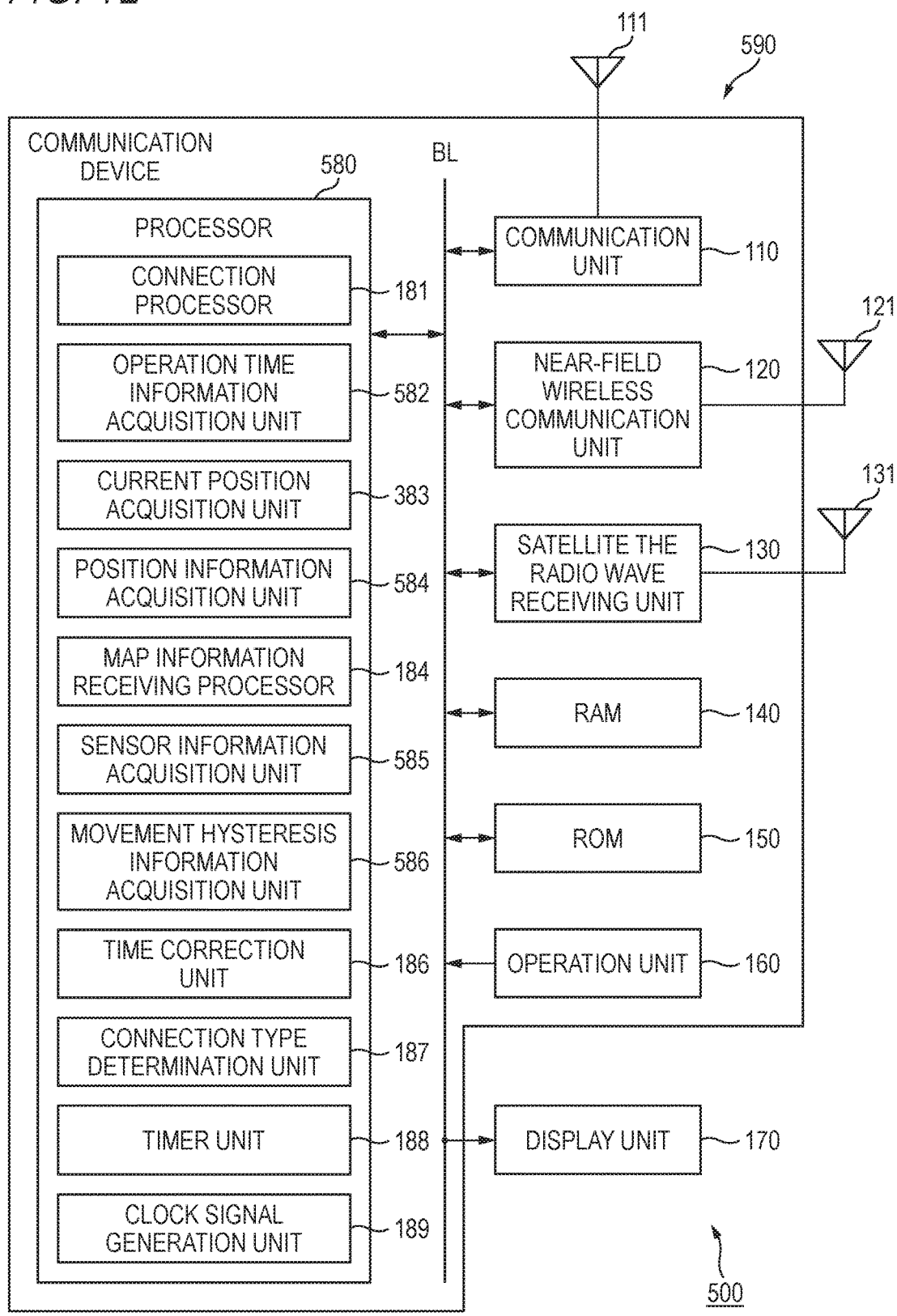
FIG. 12 is a block diagram illustrating an exemplary configuration of a smart phone according to a third illustrative embodiment.

In the below, the smart phone 500 according to the third illustrative embodiment is described. As shown in FIG. 12, the smart phone 500 includes a communication device 590 and the display unit 170. The communication device 590 includes the communication unit 110, the near-field wireless communication unit 120, the satellite radio wave receiving unit 130, the RAM 140, the ROM 150, the operation unit 160 and a processor 580. The constitutional elements of the communication device 590 and the display unit 170 are connected to each other via the bus line BL.

The smart phone 500 is different from the smart phone 100 of the first illustrative embodiment in that it includes the processor 580, instead of the processor 180. The other configurations are the same as the smart phone 100.

In the third illustrative embodiment, the ROM 150 does not store therein the data indicative of the restriction area A1 and the determination target area A2, similarly to the second illustrative embodiment. Also, in the third illustrative embodiment, the ROM 150 stores therein the program for implementing the point list generation processing and the point list, similarly to the second illustrative embodiment. That is, the smart phone 500 is configured to execute the point list generation processing shown in FIG. 10, similarly to the smart phone 300 of the second illustrative embodiment.

The processor 580 is a processor and includes a CPU. The processor 580 is configured to control an entire operation of the smart phone 500 by executing various programs stored in the ROM 150. In the below, a functional configuration of the processor 580 of the smart phone 500 is described.

The processor 580 is configured to function as the connection processor 181, an operation time information acquisition unit 582, the current position acquisition unit 383, a position information acquisition unit 584, the map information receiving processor 184, a sensor information acquisition unit 585, a movement history information acquisition unit 586, the time correction unit 186, the connection type determination unit 187, the timer unit 188, and the clock signal generation unit 189.

The operation time information acquisition unit 582 is configured to acquire the operation time information transmitted from the electronic timepiece 600. Specifically, the operation time information acquisition unit 582 is configured to control the near-field wireless communication unit 120 to receive the operation time information transmitted from the electronic timepiece 600. This operation time information is information indicative of time at which the information acquisition instruction by the proximate operation is received and which is stored in the ROM 230 by the electronic timepiece 600, similarly to the second illustrative embodiment.

The position information acquisition unit 584 is configured to acquire the position information indicative of a position at time based on the operation time information acquired by the operation time information acquisition unit 582.

Specifically, the position information acquisition unit 584 is configured to determine whether the information indicative of a position of the electronic timepiece 600 is included in acquisition information received from the electronic timepiece 600 via the near-field wireless communication unit 120. In the meantime, the acquisition information will be described later.

When the information indicative of a position of the electronic timepiece 600 is included in the acquisition information received from the electronic timepiece 600, the position information acquisition unit 584 acquires the information indicative of a position of the electronic timepiece 600, as the position information.

When the information indicative of a position of the electronic timepiece 600 is not included in the acquisition information received from the electronic timepiece 600, the position information acquisition unit 584 refers to the point list stored in the ROM 150, and acquires, as the position information, the current position associated with the acquisition time, which is closest to the time indicated by the operation time information, of the plurality of current positions included in the point list.

When sensor information is included in the acquisition information received from the electronic timepiece 600 via the near-field wireless communication unit 120, the sensor information acquisition unit 585 acquires the sensor information, which will be described later.

The movement history information acquisition unit 586 is configured to acquire the movement history information based on the plurality of map information stored in the ROM 150 by the map information receiving processor 184. The acquisition method of the movement history information by the movement history information acquisition unit 586 is substantially the same as the first illustrative embodiment and the second illustrative embodiment. However, when there is the sensor information corresponding to each time of the plurality of map information, the movement history information which is acquired by the movement history information acquisition unit 586 is information in which the sensor information and the plurality of map information are associated with each other.

In the above, the configuration of the smart phone 500 according to the third illustrative embodiment has been described. Next, a configuration of the electronic timepiece 600 according to the third illustrative embodiment is described.

Figure 13:
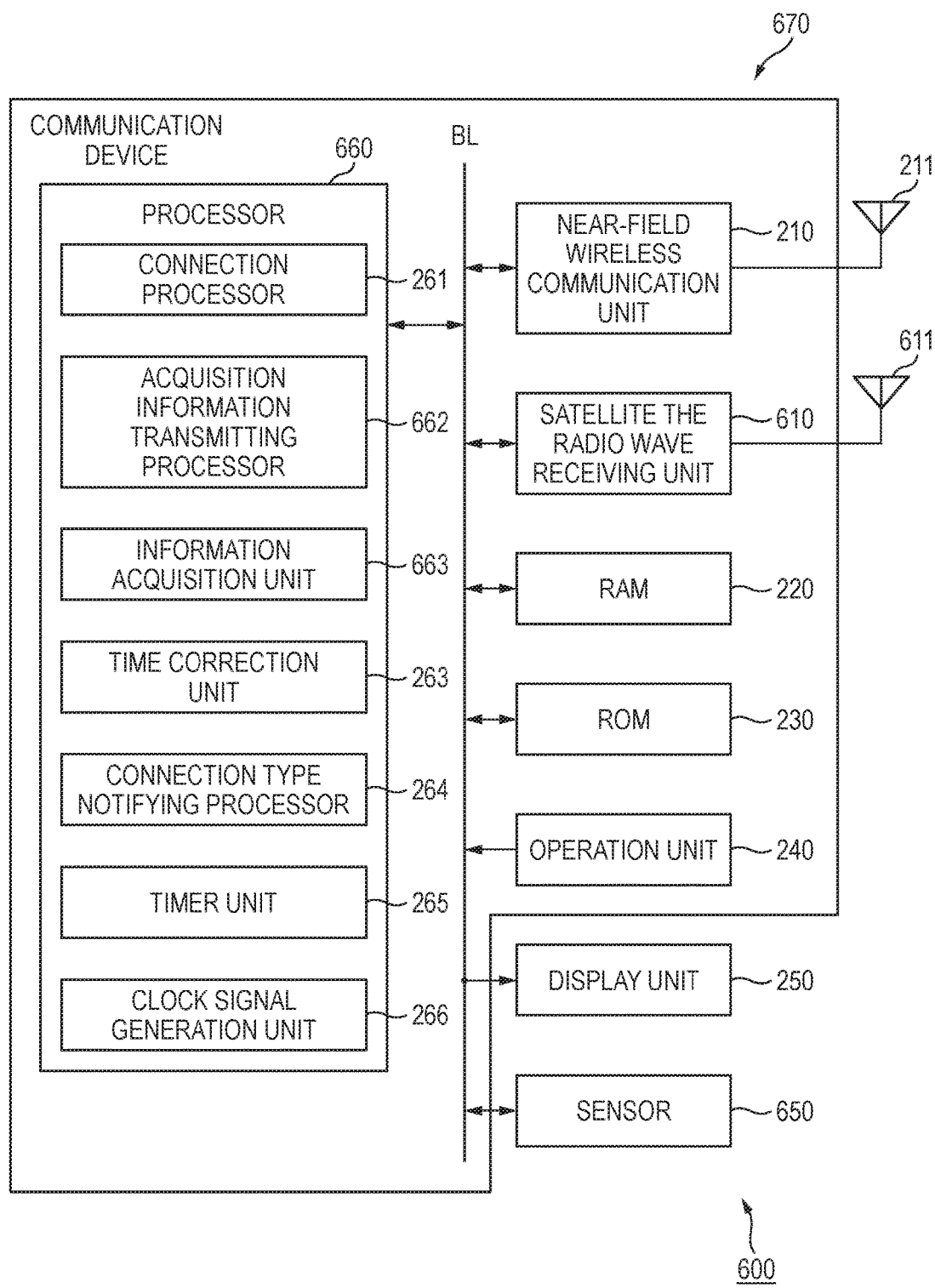
FIG. 13 is a block diagram illustrating an exemplary configuration of an electronic timepiece according to the third illustrative embodiment.

As shown in FIG. 13, the electronic timepiece 600 includes a communication device 670, the display unit 250 and a sensor 650. The communication device 670 includes the near-field wireless communication unit 210, a satellite radio wave receiving unit 610, the RAM 220, the ROM 230, the operation unit 240, and a processor 660. The constitutional elements of the communication device 670, the display unit 250 and the sensor 650 are connected to each other via the bus line BL.

The electronic timepiece 600 is different from the electronic timepiece 200 of the first illustrative embodiment in that it includes the processor 660, instead of the processor 260. Also, the electronic timepiece 600 is different from the electronic timepiece 200 of the first illustrative embodiment in that it includes the satellite radio wave receiving unit 610 and the sensor 650, which are not provided to the electronic timepiece 200. The other configurations are the same as the electronic timepiece 200.

In the third illustrative embodiment, similarly to the second illustrative embodiment, the ROM 230 also stores the operation time information, which indicates time at which a pushing operation is received, each time when the user pushes the operation button for executing the information acquisition instruction on the operation unit 240 of the electronic timepiece 600. Therefore, when the operation button for executing the information acquisition instruction is repetitively pushed, the plurality of operation time information are accumulated in the ROM 230.

The satellite radio wave receiving unit 610 includes a radio frequency circuit, a base band circuit, an LSI and the like, for example. The satellite radio wave receiving unit 610 is configured to receive a radio wave from the satellite 40 via an antenna 611.

The sensor 650 is a sensor configured to detect a temperature, an atmosphere, an altitude, a speed and the like, for example. Herein, an example where the sensor 650 is a temperature sensor is described. It is noted that the sensor 650 may be a plurality of sensors.

The processor 660 is a processor and includes a CPU. The processor 660 is configured to control an entire operation of the electronic timepiece 600 by executing various programs stored in the ROM 230.

Herein, a functional configuration of the processor 660 of the electronic timepiece 600 is described. The processor 660 is configured to function as the connection processor 261, an acquisition information transmitting processor 662, an information acquisition unit 663, the time correction unit 263, the connection type notifying processor 264, the timer unit 265, and the clock signal generation unit 266.

When the user executes an operation for transmitting the acquisition information on the operation unit 240, the acquisition information transmitting processor 662 controls the near-field wireless communication unit 210 to transmit the acquisition information stored in the ROM 230 to the smart phone 500.

The information acquisition unit 663 is configured to acquire information indicative of a current position of the electronic timepiece 600, sensor information, which is measured data of the sensor 650, and operation time information indicative of time at which the operation button for executing the information acquisition instruction is pushed.

The information acquisition unit 663 is configured to control the satellite radio wave receiving unit 610 to receive the radio wave from the satellite 40. The information acquisition unit 663 is configured to calculate a position (latitude and longitude) based on the received radio wave and to acquire the position, as the information indicative of a current position of the electronic timepiece 600. When the operation button for executing the information acquisition instruction is pushed, the information acquisition unit 663 acquires the sensor information at that time and the information indicative of the current position of the electronic timepiece 600. The information acquisition unit 663 stores the acquired sensor information and information indicative of the current position of the electronic timepiece 600 in the ROM 230 in association with the operation time information indicative of the time at that time.

Herein, the acquisition information is information acquired by the information acquisition unit 663. The acquisition information includes the operation time information, the sensor information, and the information indicative of the current position of the electronic timepiece 600. However, the sensor information and the information indicative of the current position of the electronic timepiece 600 are not included in the acquisition information when the information acquisition unit 663 cannot acquire the same. For example, upon pushing of the operation button for executing the information acquisition instruction on the operation unit 240 of the electronic timepiece 600, when the functions of the sensor 650 and the satellite radio wave receiving unit 610 are stopped, when the satellite radio wave receiving unit 610 cannot receive the radio wave from the satellite 40, and the like, the acquisition information includes only the operation time information.

Figure 14:
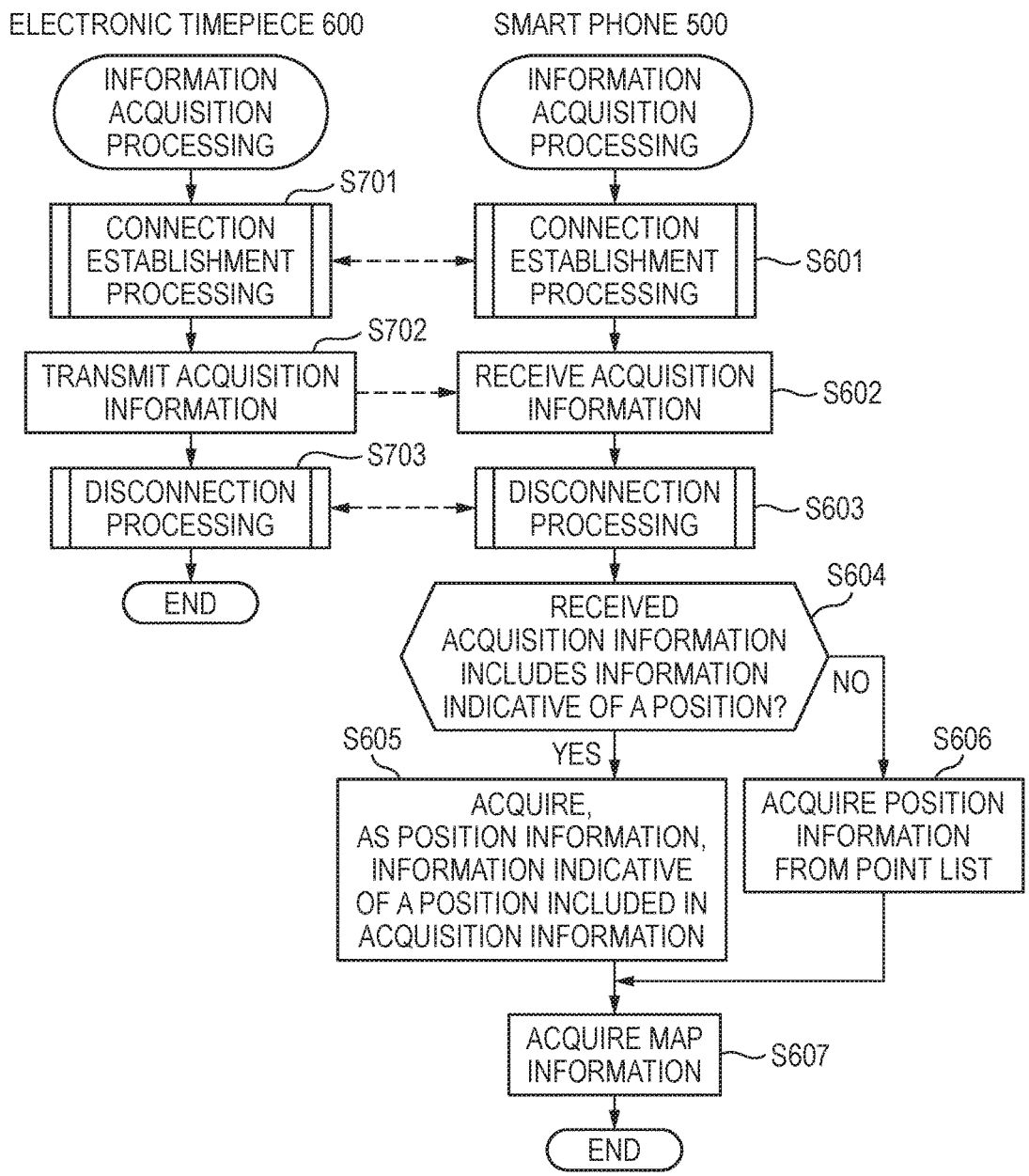
FIG. 14 is a flowchart illustrating an example of the information acquisition processing which is executed by the smart phone and the electronic timepiece according to the third illustrative embodiment.

In the above, the configuration of the electronic timepiece 600 according to the third illustrative embodiment has been described. Next, an example of the information acquisition processing which is executed by the smart phone 500 and the electronic timepiece 600 is described with reference to FIG. 14.

The information acquisition processing is executed when the user performs an operation for transmitting the operation time information stored in the ROM 230 of the electronic timepiece 600 to the smart phone 500 on the operation unit 240 of the electronic timepiece 600. The information acquisition processing may be periodically executed by the processor 660 of the electronic timepiece 600.

When the information acquisition processing is executed, connection establishment processing of establishing connection between the electronic timepiece 600 and the smart phone 500 is first executed (steps S701 and S601). This connection establishment processing is the same as the first illustrative embodiment.

When the connection between the electronic timepiece 600 and the smart phone 500 is established, the operation time information transmitting processor 662 of the electronic timepiece 600 transmits the acquisition information stored in the ROM 230 to the smart phone 500 via the near-field wireless communication unit 210 (step S702).

When a plurality of the acquisition information are stored in the ROM 230, they are all transmitted. Also, the operation time information transmitting processor 662 of the electronic timepiece 600 deletes the transmitted acquisition information from the acquisition information stored in the ROM 230.

The processor 580 of the smart phone 500 receives the acquisition information transmitted from the electronic timepiece 600, via the near-field wireless communication unit 120 (step S602). The operation time information acquisition unit 582 of the smart phone 500 acquires the operation time information included in the received acquisition information. When the sensor information is included in the received acquisition information, the sensor information acquisition unit 585 of the smart phone 500 acquires the sensor information.

Herein, disconnection processing of disconnecting the connection between the electronic timepiece 600 and the smart phone 500 is executed (steps S403 and S503). This disconnection processing is the same as the first illustrative embodiment.

Then, the position information acquisition unit 584 of the smart phone 500 determines whether the information indicative of a position of the electronic timepiece 600 is included in the acquisition information received from the electronic timepiece 600 via the near-field wireless communication unit 120 (step S604). The acquisition information will be described later.

When it is determined that the information indicative of a position of the electronic timepiece 600 is included in the acquisition information received from the electronic timepiece 600 (step S604; Yes), the position information acquisition unit 584 acquires, as the position information, the information indicative of a position of the electronic timepiece 600 and included in the acquisition information (step S605).

On the other hand, when it is determined that the information indicative of a position of the electronic timepiece 600 is not included in the acquisition information received from the electronic timepiece 600 (step S604; No), the position information acquisition unit 584 refers to the point list stored in the ROM 150, and acquires, as the position information, the current position associated with the acquisition time, which is closest to the time indicated by the operation time information, of the plurality of current positions included in the point list (step S606).

In the meantime, when a plurality of acquisition information are received from the electronic timepiece 600, the position information acquisition unit 584 acquires the plurality of position information corresponding to the plurality of operation time information included in the plurality of acquisition information.

Subsequently, the map information receiving processor 184 of the smart phone 500 receives and acquires the map information corresponding to the position information acquired by the position information acquisition unit 584, from the map information distribution server 60, via the communication unit 110 (step S607). When the position information acquisition unit 584 acquires the plurality of position information, the map information receiving processor 184 acquires the plurality of map information corresponding to the plurality of position information.

The processor 580 of the smart phone 500 stores the map information acquired by the map information receiving processor 184, in the ROM 150 in association with the time indicated by the operation time information acquired by the operation time information acquisition unit 582. When the sensor information is included in the acquisition information, the processor 580 of the smart phone 500 further stores the sensor information acquired by the sensor information acquisition unit 585, in the ROM 150 in association with the map information and the time indicated by the operation time information.

The movement history information acquisition unit 586 of the smart phone 500 acquires the movement history information based on the plurality of map information stored in the ROM 150, similarly to the first and second illustrative embodiments. When there is the sensor information associated with the plurality of map information, the information is also associated with the movement history information.

As described above, in the third illustrative embodiment, the smart phone 500 can acquire the map information with which the sensor information acquired by the electronic timepiece 600 is also associated. Also, the electronic timepiece 600 acquires the position of the electronic timepiece 600 at time at which the operation button for executing the information acquisition instruction is pushed. In this case, since the smart phone 500 acquires the map information based on the position acquired by the electronic timepiece 600, the map information can be acquired at user's intended timing more correctly than the first illustrative embodiment.

Although the illustrative embodiments have been described, the illustrative embodiments are merely exemplary. Accordingly, the specific configurations and processing of the smart phones 100, 300, 500 and the electronic timepieces 200, 400, 600 are not limited to the illustrative embodiments. In the below, modified embodiments of the illustrative embodiments are described.

(Modified Embodiments)

In the illustrative embodiments, as the wireless communication device and the other wireless communication device, the smart phones 100, 300, 500 and the electronic timepieces 200, 400, 600 have been exemplified. However, the wireless communication device and the other wireless communication device are not limited to the smart phone and the electronic timepiece.

For example, a portable terminal having a wireless communication function based on the BLE such as a portable phone, a smart phone, a tablet-type personal computer, a note-type personal computer and the like may also be used. As the wireless communication device which is used instead of the electronic timepiece, a small device which can be carried and operated by a user such as a wearable computer is preferable so as to secure the high operability.

In the illustrative embodiments, the smart phones 100, 300, 500 are configured such that the processors 180, 380, 580 function as the timer unit 188 and the clock signal generation unit 189, and the electronic timepieces 200, 400, 600 are configured such that the processors 260, 460, 660 function as the timer unit 265 and the clock signal generation unit 266. However, the present disclosure is not limited thereto.

For example, the timer units 188, 265 and the clock signal generation units 189, 266 may be configured as Real Time Clock (RTC) modules separate from the processors 180,380, 580,260,460,660. The RTC module may include a counter circuit configured to count the number of pulses of the clock signal of the own device, a crystal oscillator configured to generate a reference clock, a variable Phase Locked Loop (PLL) configured to generate a clock signal having a desired frequency from the reference clock, or the like.

The constitutional elements of the first illustrative embodiment, the second illustrative embodiment and the third illustrative embodiment can be appropriately combined as long as the contradiction does not occur. For example, in the second illustrative embodiment or the third illustrative embodiment, the smart phones 300, 500 and the electronic timepieces 400, 600 may be configured to acquire the map information only when they are located outside the restriction area A1, similarly to the first illustrative embodiment.

In the third illustrative embodiment, the electronic timepiece 600 includes the sensor 650. However, the smart phone 500 may include a sensor and may be configured to acquire the sensor information at time indicated by the operation time information.

In the illustrative embodiments, the smart phones 100, 300, 500 and the electronic timepieces 200, 400, 500 are configured to store the acquired data in the ROM 150 and the ROM 230. However, the present disclosure is not limited thereto. The acquired data may be stored in the RAM 140 and the RAM 220, not in the ROM 150 and the ROM 230. That is, the storing destination may be any storage device such as the RAM, the ROM and the like.

In the illustrative embodiments, the functional configuration of the processors 180, 260, 380, 460, 580, 660 may be a single processor, as in the third illustrative embodiment, or may be a plurality of processors.

In the illustrative embodiments, the wireless communication devices configured to perform wireless communication based on the BLE have been exemplified. However, the present disclosure is not limited to the wireless communication device configured to perform wireless communication based on the BLE. For example, the present disclosure may also be applied to a wireless communication device configured to perform wireless communication based on Wi-Fi (registered trademark), ZigBee (registered trademark) or the like.

Also, the wireless communication device of the present disclosure may be configured such that a computer executes a program to implement the functions of the smart phones 100, 300, 500 and the electronic timepieces 200, 400, 600, irrespective of the wireless communication device. The program may be stored in a computer-readable recording medium such as a Universal Serial Bus (USB) memory, a Compact Disc-Read Only Memory (CD-ROM), a Digital Versatile Disc (DVD), a Hard Disc Drive (HDD) and the like, or may be downloaded to the computer via a network.

In the illustrative embodiments, the smart phones 100, 300, 500 are configured to acquire the time information from the NTP server 10. However, the present disclosure is not limited thereto. The smart phone 100 may be configured to acquire the time information from a time server prescribed by the other protocol, such as an Simple Network Time Protocol (SNTP) server, for example.

In the illustrative embodiments, the map information receiving processor 184 is configured to receive the map information via the communication unit 110. However, the map information receiving processor 184 may be changed to the map information acquisition unit. The map information acquisition unit may be configured to generate and acquire the map information based on image data stored in the ROM 150 and data received via the communication unit 110, for example.

Also, in the illustrative embodiments, as long as there is no technical contradiction, "acquisition" may be an operation of acquiring data received from an external device or other constitutional element or may be an operation of acquiring data generated based on data received from an external device or other constitutional element. For example, the position information acquisition units 183, 384, 584 may be configured to acquire, as the position information, data received via the communication unit 110, or may be configured to acquire, as the position information, data calculated or generated based on data received via the communication unit 110.

Although the illustrative embodiments of the present disclosure have been described, the present disclosure is not limited to the specific illustrative embodiments, and includes the inventions defined in the claims and equivalents thereto.

The invention claimed is:

1. An information acquisition method of a wireless communication device, the wireless communication device including a receiver configured to perform wireless communication with another wireless communication device to acquire information and a storage unit, and the information acquisition method comprising:
an operation time information acquisition step of acquiring operation time information indicative of a time at which the other wireless communication device receives an information acquisition instruction by an operation;
an information acquisition instruction time acquisition step of acquiring the time at which the other wireless communication device receives the information acquisition instruction based on the operation time information acquired in the operation time information acquisition step;
a position information acquisition step of acquiring position information indicative of a user position at the time at which the other wireless communication device receives the information acquisition instruction, acquired in the information acquisition instruction time acquisition step;
a map information acquisition step of acquiring map information for indicating, on a map, the position information acquired in the position information acquisition step; and
a map storing step of storing, in the storage unit, the map information acquired in the map information acquisition step, such that the map information is tied with the time at which the other wireless communication device receives the information acquisition instruction, acquired in the information acquisition instruction time acquisition step.

2. The information acquisition method according to claim 1, further comprising:
a movement history information acquisition step of acquiring movement history information based on a plurality of the map information stored in the map storing step.

3. The information acquisition method according to claim 1, wherein the position information acquisition step acquires, as the position information, a current position of the wireless communication device when the operation time information is acquired in the operation time information acquisition step.

4. The information acquisition method according to claim 2, wherein the position information acquisition step acquires, as the position information, a current position of the wireless communication device when the operation time information is acquired in the operation time information acquisition step.

5. The information acquisition method according to claim 1, further comprising:
a current position acquisition step of periodically acquiring a current position of the wireless communication device; and
a position storing step of storing, in the storage unit, the current position acquired in the current position acquisition step such that the current position is tied with an acquisition time thereof,
wherein the position information acquisition step acquires, as the position information, the current position tied with an acquisition time which is closest to the time at which the other wireless communication device receives the information acquisition instruction, acquired in information acquisition instruction time acquisition, from among a plurality of the current positions stored in the position storing step and acquired in the current position acquisition step which are periodically repeated.

6. The information acquisition method according to claim 1, wherein the position information acquisition step controls the receiver to receive information indicative of a position of the other wireless communication device transmitted from the other wireless communication device and acquires, as the position information, the received information indicative of the position of the other wireless communication device.

7. The information acquisition method according to claim 2, wherein the position information acquisition step controls the receiver to receive information indicative of a position of the other wireless communication device transmitted from the other wireless communication device and acquires, as the position information, the received information indicative of the position of the other wireless communication device.

8. The information acquisition method according to claim 1, further comprising:
a sensor information acquisition step of acquiring sensor information at the time at which the other wireless communication device receives the information acquisition instruction, acquired in information acquisition instruction time acquisition step.

9. The information acquisition method according to claim 2, further comprising:
a sensor information acquisition step of acquiring sensor information at the time at which the other wireless communication device receives the information acquisition instruction, acquired in information acquisition instruction time acquisition step.

10. The information acquisition method according to claim 3, further comprising:
a sensor information acquisition step of acquiring sensor information at the time at which the other wireless communication device receives the information acquisition instruction, acquired in information acquisition instruction time acquisition step.

11. The information acquisition method according to claim 4, further comprising:
a sensor information acquisition step of acquiring sensor information at the time at which the other wireless communication device receives the information acquisition instruction, acquired in information acquisition instruction time acquisition step.

12. The information acquisition method according to claim 5, further comprising:
a sensor information acquisition step of acquiring sensor information at the time at which the other wireless communication device receives the information acquisition instruction, acquired in information acquisition instruction time acquisition step.

13. The information acquisition method according to claim 6, further comprising:
a sensor information acquisition step of acquiring sensor information at the time at which the other wireless communication device receives the information acquisition instruction, acquired in information acquisition instruction time acquisition step.

14. The information acquisition method according to claim 7, further comprising:
a sensor information acquisition step of acquiring sensor information at the time at which the other wireless communication device receives the information acquisition instruction, acquired in information acquisition instruction time acquisition step.

15. The information acquisition method according to claim 1, wherein the wireless communication device further includes a display unit, and
wherein the information acquisition method further comprises:
a display step of displaying, on the display unit, the position information and the map information acquired in the map information acquisition step when the position information, acquired in the position information acquisition step, is outside a predetermined restriction area.

16. A wireless communication device comprising:
a receiver that performs wireless communication with another wireless communication device;
a storage unit; and
a processor that:
acquires operation time information transmitted from the other wireless communication device and indicative of a time at which the other wireless communication device receives an information acquisition instruction by an operation;
acquires the time at which the other wireless communication device receives the information acquisition instruction based on the operation time information;
acquires position information indicative of a user position at the time at which the other wireless communication device receives the information acquisition instruction;
acquires map information for indicating, on a map, the acquired position information; and
stores, in the storage unit, the map information such that the map information is tied with the time at which the other wireless communication device receives the information acquisition instruction.

17. A non-transitory computer-readable recording medium having a program recorded therein, the program being readable by a computer of a wireless communication device including a receiver configured to perform wireless communication with another wireless communication device and a storage unit, and the program, when executed by the computer, causing the computer to:
control the receiver to acquire operation time information indicative of a time at which the other wireless communication device receives an information acquisition instruction by an operation;
acquire the time at which the other wireless communication device receives the information acquisition instruction based on the operation time information;
acquire position information indicative of a user position at the time at which the other wireless communication device receives the information acquisition instruction;
controls the receiver to receive map information for indicating, on a map, the acquired position information; and
stores, in the storage unit, the map information such that the map information is tied with the time at which the other wireless communication device receives the information acquisition instruction.

* * * * *